(12) United States Patent
Wallach et al.

(10) Patent No.: US 6,904,434 B1
(45) Date of Patent: Jun. 7, 2005

(54) METHOD AND SYSTEM FOR PROVIDING REAL-TIME CLINICAL TRIAL ENROLLMENT DATA

(75) Inventors: Matt Wallach, New York, NY (US); Rachel Yang, Florham Park, NJ (US); Prasad Inampudi, Jersey City, NJ (US); Sathya Thulsidas, Parsippany, NJ (US); Sheela Sundaresan, Morris Plains, NJ (US)

(73) Assignee: Siebel Systems, Inc., San Mateo, CA (US)

( * ) Notice: Subject to any disclaimer, the term of this patent is extended or adjusted under 35 U.S.C. 154(b) by 532 days.

(21) Appl. No.: 10/024,857

(22) Filed: Dec. 18, 2001

(51) Int. Cl.[7] ............................................. G06F 17/30
(52) U.S. Cl. ..................... 707/10; 707/102; 707/104; 707/1
(58) Field of Search ............................. 707/1, 10, 102, 707/104, 100, 3; 600/509, 407; 705/2; 435/6; 702/19; 706/21

(56) References Cited

U.S. PATENT DOCUMENTS

| | | | | |
|---|---|---|---|---|
| 6,098,047 A | * | 8/2000 | Oku et al. ....................... 705/7 |
| 6,317,731 B1 | * | 11/2001 | Luciano ........................ 706/21 |
| 6,556,999 B1 | * | 4/2003 | Kloos et al. ................... 707/10 |
| 6,708,057 B2 | * | 3/2004 | Morganroth ................ 600/509 |
| 2002/0012921 A1 | * | 1/2002 | Stanton, Jr. ..................... 435/6 |
| 2002/0095258 A1 | * | 7/2002 | Agur et al. .................... 702/19 |
| 2003/0013951 A1 | * | 1/2003 | Stefanescu et al. .......... 600/407 |
| 2003/0065669 A1 | * | 4/2003 | Kahn et al. .................. 707/100 |
| 2003/0097077 A1 | * | 5/2003 | Morganroth ................ 600/509 |
| 2003/0097220 A1 | * | 5/2003 | Agur et al. .................... 702/19 |
| 2003/0208378 A1 | * | 11/2003 | Thangaraj et al. .............. 705/2 |
| 2004/0006553 A1 | * | 1/2004 | de Vries et al. ................ 707/1 |
| 2004/0082000 A1 | * | 4/2004 | Stanton, Jr. ..................... 435/6 |

* cited by examiner

Primary Examiner—Thuy N. Pardo
(74) Attorney, Agent, or Firm—Blakely, Sokoloff, Taylor & Zafman LLP; James W. Soong

(57) ABSTRACT

A method and system for enabling display of real-time clinical trial enrollment data. A set of computer forms corresponding to an application enable administrative personnel to define a plurality of clinical trial parameters, including trial protocols, clinical sites, and optional regions. As the data is entered, it is stored in a central database, typically through a dedicated connection between a client running the application and the database. Software and infrastructure for supporting an Internet web portal is also provided, whereby the web portal enables clinical site personnel to enter subject enrollment data that is stored in the database as it is entered (i.e., in real-time). Various charts pertaining to the subject enrollment data may then be generated, including subject status charts and subject enrollment rate charts. In general, the charts may be aggregated across individual sites, regions, and all sites corresponding to a given protocol.

24 Claims, 19 Drawing Sheets

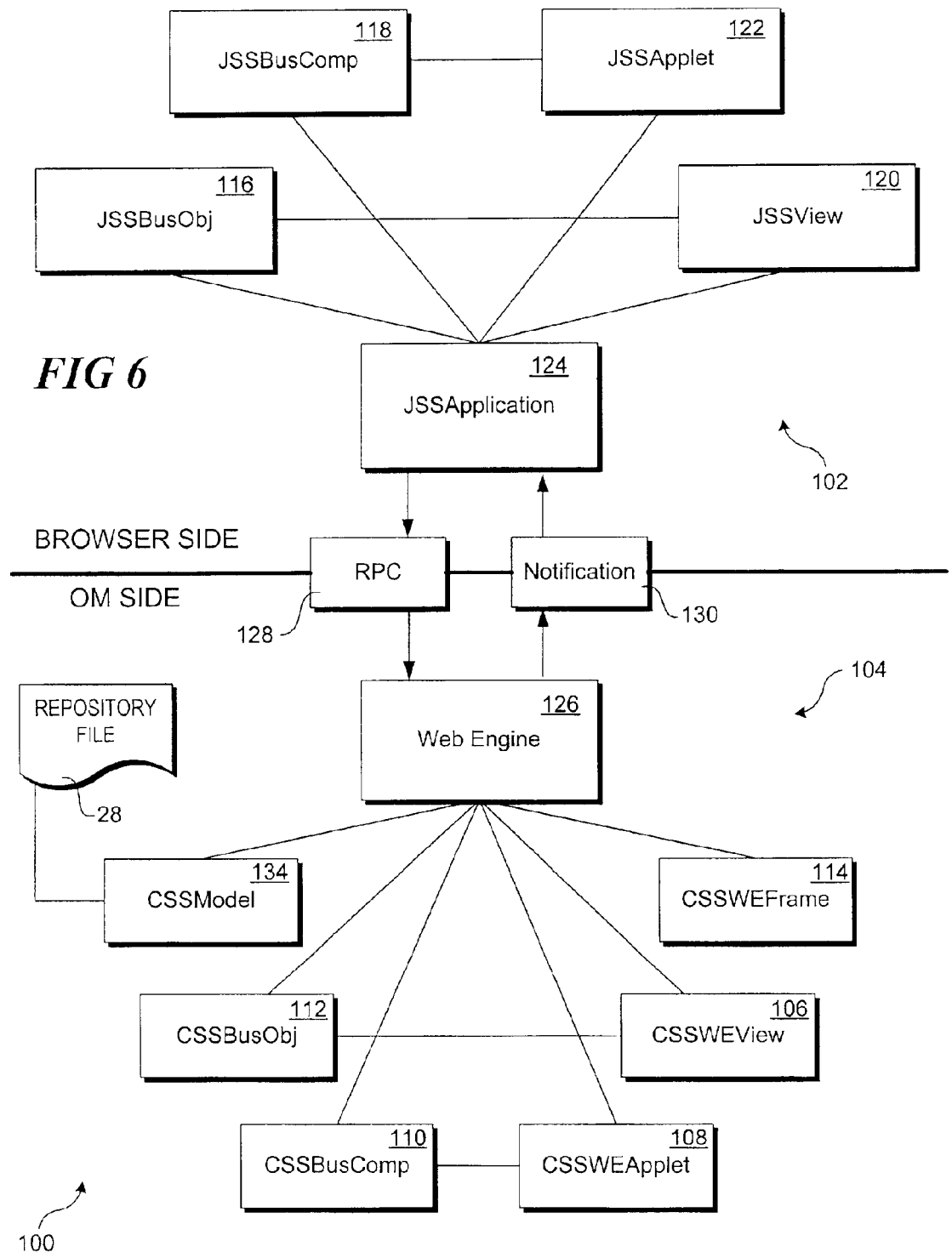

METHOD AND SYSTEM FOR PROVIDING REAL-TIME CLINICAL TRIAL ENROLLMENT DATA

BACKGROUND OF THE INVENTION

1. Field of the Invention

The present invention generally pertains to software and systems for managing clinical trials, and, in more particular, concerns a method and system for providing real-time clinical trial enrollment data via a distributed software architecture.

2. Background Information

Clinical trials are a critical aspect in the development of any new drug, and are also used to verify the safety and efficacy of treatment modalities, such as new surgical techniques. For example, in order to obtain FDA (Federal Food and Drug Administration) approval, the safety, efficacy and other effects of an investigational drug are evaluated through observation and survey of various test subjects who are provided with the drug (or concurrent controls, such as a placebo) during clinical trials of the drug. Typically, clinical trials take several years and cost millions of dollars.

Clinical trials typically involve three phases, named Phase I, Phase II, and Phase III. The process starts when a sponsor files an application, called Investigational New Drug Application (IND), to conduct a Phase I clinical trial on human subjects. Absence of objection, the Phase I clinical trial(s) are performed. Phase I trials typically involve a small group of test subjects (e.g., less than 50), and are primarily designed to characterize the performance of the drug, with emphasis on safety. Generally, the subjects participating in a Phase I clinical trial are healthy volunteers, A Phase I trial is designed to determine what happens to the drug in the human body—how it is absorbed, metabolized, and excreted. A Phase I study will investigate side effects that occur as dosage levels are increased. Administration of Phase I studies are typically performed at a very small number of sites, such as a few (or even one) research hospitals.

If the drug is shown to be safe (based on Phase I human trials and toxicology tests on animals), the sponsor will move on toPhase II clinical trials using a larger subject group. Phase II is designed to show the efficacy of the drug, and is typically performed with several hundreds of subjects, using a small to moderate number of sites. Phase II trails are usually controlled studies, using one or more concurrent controls, such as dosage comparison, placebo, no-treatment, active treatment, and historical control.

If the results of Phase II show promise, the sponsor will move on to Phase III trials. Phase III clinical trials are designed to project the behavior of the drug on large targeted populations, including efficacy, safety, and side effects. One reason for Phase III trials is to statistically remove (ideally) any anomalies that may result from a Phase II study group that doesn't adequately represent a cross-section of the population targeted for the drug. Accordingly, Phase III studies are carried on larger subject populations (typically 500–2000+), preferably using a significant number of geographically-disperse and/or ethnically-diverse sites so that the results of the clinical trial better reflect the actual effects on the targeted population in response to taking the drug.

Each clinical trial is managed by a sponsor, comprising an individual, company, institution, or organization that also takes responsibility for the initiation and/or financing of the clinical trial. Typically, the sponsor will be a pharmaceutical or biotech company, or other entity that has developed the drug, or has a substantial interest in the drug or an existing drug proposed for a new use. Sponsors are also responsible for applying to regulatory agencies for permission to conduct clinical trails on human subjects, filing the results of the trials, and applying for FDA approval at the end of the clinical trials. These tasks are typically performed by a team, including a clinical director, clinical manager, and one or more clinical research associates (CRAs).

Each clinical trial is conducted in accordance with a protocol. A protocol is a document that describes the objective(s), design, methodology, statistical considerations, and organization of a trial. The protocol states what will be done in the study and why. It outlines how many subjects will take part in the study, what types of subjects may take part, what tests they will receive and how often, and the treatment plan. The trial protocols are typically written by clinical trial administrators and other personnel working for the sponsor based on standardized and mandated methodologies and input from physicians who specialize in medical areas pertaining to the drug's intended use. Oftentimes, the protocol for a given phase will change over the course of the trial, based on information derived from earlier testing, leading to Protocol Amendments or Protocol Addendi.

The actual tests identified by the protocol are administered and monitored by qualified medical professionals (known as investigators), who are often physicians, and their staffs (e.g., nurse practitioners). An investigator is the person responsible for the conduct of the clinical trial at a trial site. If a trial is conducted by a team of individuals at a given site, the investigator who is the responsible leader of the team is called the principal investigator. A site is a team of individuals, headed by a principal investigator, who conduct clinical trials based on a protocol in specified locations, called sites.

Typically, each CRA is assigned to manage one or more investigators at one or more sites to ensure clinical trial is conducted in accordance with regulatory guidance and Good Clinical Practice (GCP). Examples of the tasks normally perform by CRA are: collecting regulatory documents, conducting site visits to retrieve Case Report Form, and writing trip reports.

SUMMARY OF THE INVENTION

A method and system for enabling display of real-time clinical trial enrollment data via user-configured charts. A set of computer forms corresponding to an eClinical computer application enable administrative personnel to define a plurality of clinical trial parameters, including parameters pertaining to programs, protocols, clinical sites, and regions. In one embodiment, the application is run on a dedicated client that has a dedicated connection to an enterprise (i.e., central) database. As the clinical trial parameters are entered and saved, corresponding data is stored in the enterprise database. Software and infrastructure for supporting an Internet web portal is also provided, whereby web portal users, such as clinical site personnel are enabled to enter and store various data pertaining to clinical trials they are involved with, including subject enrollment data. Upon user authentication, users are enabled to navigate to and fill various forms, wherein the data entered into the forms are mapped to clinical trial sites and protocols specific to the user and/or the user's position. As the data is entered, it is stored in the enterprise database, substantially in real-time.

Various charts pertaining to the subject enrollment data may then be generated based on the data in the enterprise database, including subject status charts and subject enrollment rate charts. In general, the charts may be aggregated across individual sites, regions, and all sites corresponding to a given protocol, based on user selected options.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 6 is a block schematic diagram illustrating a system framework comprising a set of browser-side object classes from which browser side objects are derived that interact with a set of object manager managed objects defined by a corresponding set of object classes;

FIG. 11 is a representation of a protocol view that enables clinical trial protocol parameters to be entered via the eClinical application;

FIG. 12 is a representation of a regions view that enables protocol sites to be grouped by selected regions;

FIG. 14 is a representation of a web portal home page from which a web portal is enabled to navigate to various data pertaining to clinical trials the user participates in or manages;

FIG. 15 is a view that enables a user to enter, screen, and enroll clinical trial subjects;

DETAILED DESCRIPTION OF THE ILLUSTRATED EMBODIMENTS

A system and method for providing real-time clinical trial subject enrollment data is described in detail herein. In the following description, numerous specific details are disclosed, such as various user architectures, user interfaces, and charts, to provide a thorough understanding of embodiments of the invention. One skilled in the relevant art will recognize, however, that the invention can be practiced without one or more of the specific details, or with other methods, components, etc. In other instances, well-known structures or operations are not shown or described in detail to avoid obscuring aspects of various embodiments of the invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

System Overview and Architecture

The present invention enables various clinical trial participants, such as CRAs, real-time access to clinical trial subject enrollment data pertaining to various clinical trial parameters, such as protocols, sites, and regions. The system enables investigators (and/or other site personnel) to enter clinical trial data via an Internet web portal using web-based user-interface (UI) forms. This information is stored in a central "enterprise" database that can be accessed by CRAs and other users via a dedicated or web-based connection. A set of software tools are provided to enable the users to view various tabulated and chart information pertaining to the clinical trial data.

Figure 1:
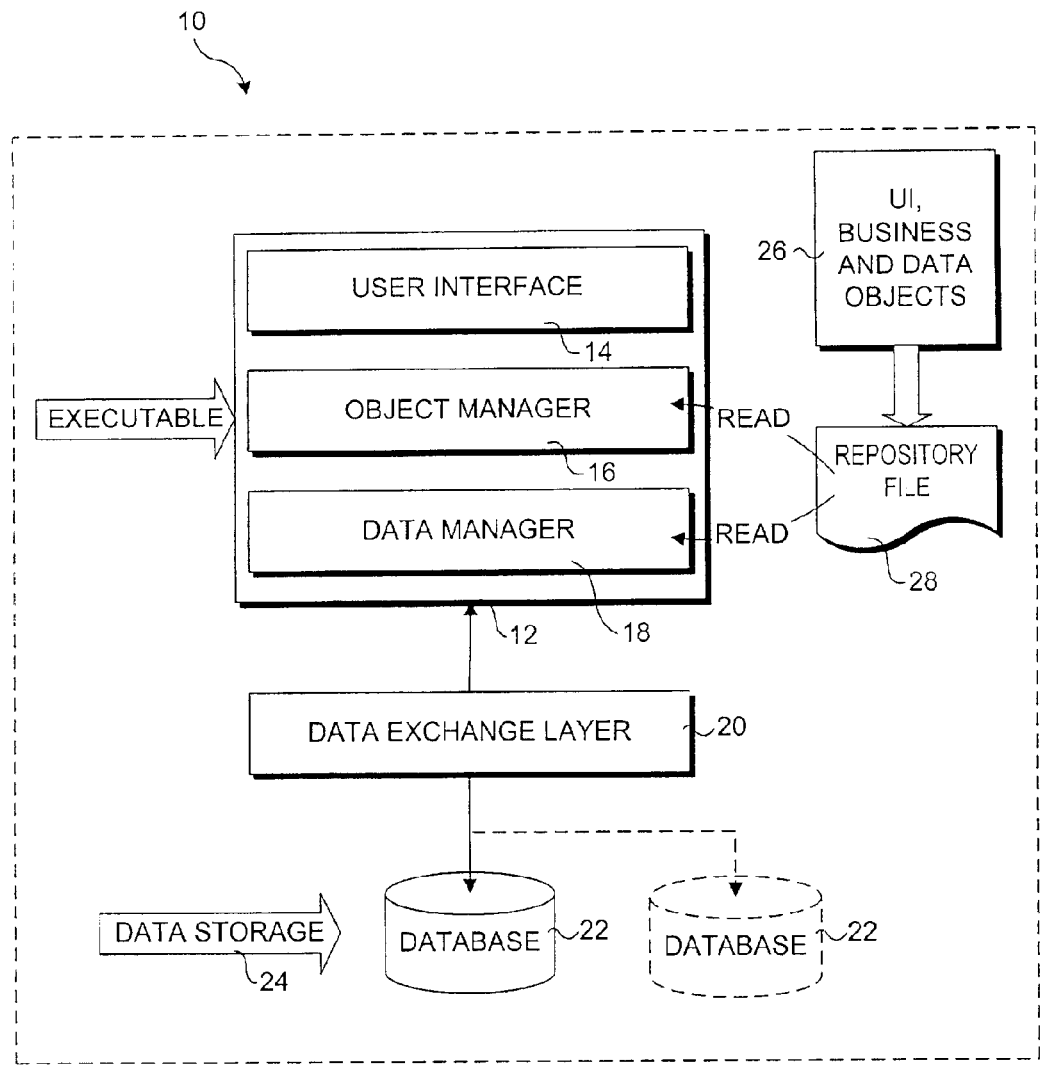
FIG. 1 is a block schematic diagram illustrating an exemplary high-level logical multi-layer architecture by which the invention may be implemented.

In one embodiment, a system in which the teachings of the present invention are implemented can be logically structured as a multi-layered architecture 10, as shown in FIG. 1. In one embodiment, the logical multi-layered architecture provides a platform for common services 12 to support various applications that implement the architecture. These services may include a user interface layer 14, an object manager layer 16, a data manager layer 18, and a data exchange layer 20.

In one embodiment, user interface layer 14 may provide the applets, views, charts and reports, etc. associated with one or more applications. Generally, user interface layer 14 may be configured to support various types of clients, including traditional connected clients, remote clients, thin clients over an Intranet, Java thin clients or non-Windows-based operating systems, and HTML clients over the Internet, etc.

Object manager layer 16 is designed to manage one or more sets of business rules or business concepts associated with one or more applications and to provide the interface between user interface layer 14 and data manager layer 18. In one embodiment, the business rules or concepts can be represented as business objects. In one embodiment, the business objects may be designed as configurable software representations of the various business rules or concepts applicable to the real-time clinical data services provided by the invention.

Data manager layer 18 is designed to maintain logical views of underlying data stored in one or more databases 22 corresponding to a data storage layer 24, while allowing the object manager to function independently of the underlying data structures or tables in which data are stored. In one embodiment, the data manager provides certain database query functions, such as generation of structure query language (SQL) in real time to access the data. In one embodiment, data manager 18 is designed to operate on object definitions 26 stored in a repository file 28 corresponding to a database schema used to implement that data model for the system, as described in further detail below. Generally, the data exchange layer is designed to handle the interactions with one or more specific target databases and provide the interface between the data manager and those databases, via either generic (Open Database Connectivity (ODBC)) or native (e.g., Oracle Connection Interface (OCI)) database interface protocols.

Figure 2:
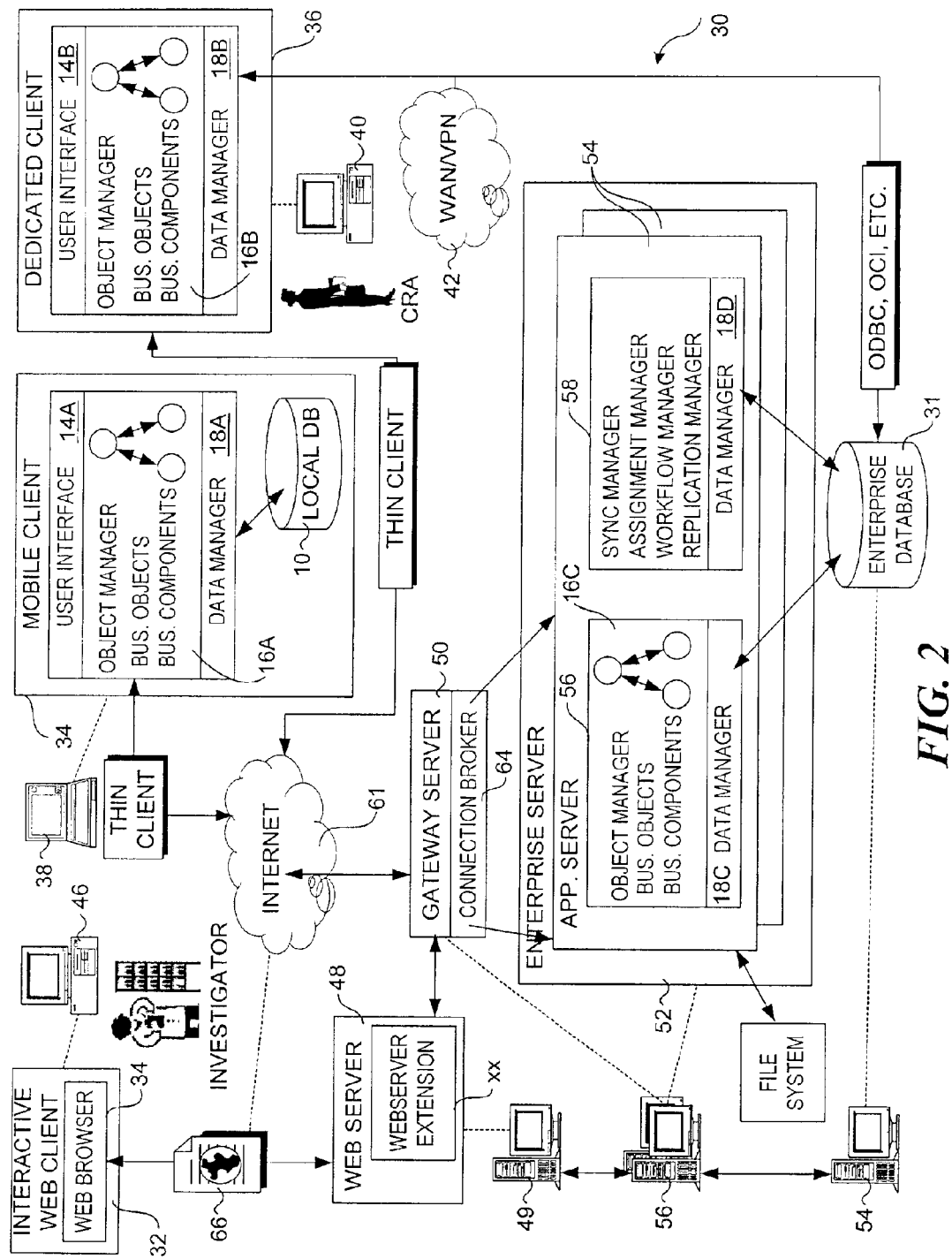
FIG. 2 is a block schematic diagram illustrating a system architecture by which the invention may be implemented.

An exemplary system architecture 30 in accordance with one embodiment of the invention is depicted in FIG. 2. Under this system architecture, various clients are able to access data stored in an enterprise database 31 via a distributed set of software components corresponding to the multi-layer architecture 10 of FIG. 1. These clients include an interactive web client 32, a mobile client 34, and a dedicated client 36, which is also called a connected client. Each of mobile client 34 and dedicated client 36 comprise respective sets of services similar to services 12 discussed above, including user interfaces 14A and 14B, object managers 16A and 16B, and data managers 18A and 18B, respectively running on a laptop computer 38 and a desktop computer 40. Interactive web client 32 includes a web browser 44 running on a desktop computer 46. It is noted the desktop and laptop computers illustrated in FIG. 2 are merely exemplary, as either desktop, workstations, or laptop computers may be used for any of interactive web client 32, mobile client 34 and dedicated client 36.

The server side of system architecture 30 is depicted as a well-known n-tier architecture, including a web server tier 48 hosted on a web server 48, a gateway server tier including a gateway server 50, an enterprise server tier provided by an enterprise server 52, and a "backend" database tier corresponding to a database server 54 that hosts enterprise database 31. In one embodiment, enterprise server 52 comprises a logical grouping of one or more application server instances 56 that connect to a common database (e.g., database 31) and point to a common gateway server (e.g., gateway server 50). In one embodiment, each application server instance will be run on a respective application server 56, and comprise a respective set of services 56 including an object manager 16C and a data manager 18C. In one embodiment, each of application server instances 54 further include additional services 58, including a synchronization manager, an assignment manager, a workflow manager, a replication manager, as well as a data manager 18D.

As shown in FIG. 2, dedicated client 36 is directly connected to enterprise database 31 via a dedicated network connection 42, such as a WAN (Wide Area Network) or VPN (Virtual Private Network) connection. Typically, data manager 18B will interface with enterprise database 31 using a standard database connection protocol, such as an ODBC or OCI over a TCP/IP connection. This allows dedicated web clients to directly access data in enterprise database 31 as if the database was a local database.

In a somewhat similar manner, mobile client 34 may be directly connected to a local database 60 hosted by the computer running the mobile web client and database server software for hosting the local database (e.g., laptop computer 38). Although directly connected internally (i.e., no network connection is required), a standard network-based database connection protocol is still used (e.g., ODBC over TCP/IP). The data stored on local database 60 will typically comprise a subset of the data in enterprise database 31. Generally, as users of mobile clients enter new data the data are be stored in local database 60, although a connection path may be provided via a network, such as Internet 61, to enable the data to be stored in enterprise database 31. Preferably, the subset of data on local database 60 should substantially replicate a corresponding subset of data on enterprise database 31. Accordingly, these subsets of data will be synchronized between the two database, when necessary or based on a predetermined criteria, using synchronization and replication services provided by the synchronization manager and the replication manager.

In one embodiment, architecture 30 further includes a file system 62 comprising a network-accessible directory that will typically be located on a storage device hosted by one of the system's application servers. Generally, file system 62 may be used to store text files corresponding to data generated by system components that are not stored in enterprise database 31. In one embodiment, dedicated clients 36 can read and write file data directly to and from the file system. In one embodiment, mobile clients 34 may have a similar local file system (not shown), which is synchronized with file system 62 on a periodic or as-needed basis.

In one embodiment, gateway server 50 is configured as a logical entity that serves as a single entry point for accessing application servers 54. Depending on the underlying application server configuration, the gateway server may include software and/or hardware services to provide enhanced scalability, load balancing, and high availability across enterprise server 52. For example, the gateway server may include a name server and a connection broker 64. In one embodiment, the name server is configured to monitor various parameters corresponding to application servers 54, such as availability and connectivity information. The various components in the system can then query the name server for various information regarding the application servers' availability and connectivity. In one embodiment, connection broker 64 is used to perform load balancing, wherein new client requests are directed (preferably) to a least busy server.

As explained in further detail below, web server 48 serves interactive web pages 64 that may be access via a web portal, i.e., a URL-based Internet address. Interactive web pages 64 are based on HTML data, applets, and other UI components generated by enterprise server 52, with further assistance from a web extension component 66. These web pages are termed "interactive" because the content they display are dependent on clinical data parameters pertaining to a current user of the web page. Furthermore, in one embodiment, the user interface components of both the mobile client and dedicated client are HTML-based interfaces that are rendered by an appropriate browser running on each of laptop computer 38 and desktop computer 40, respectively.

Figure 3:
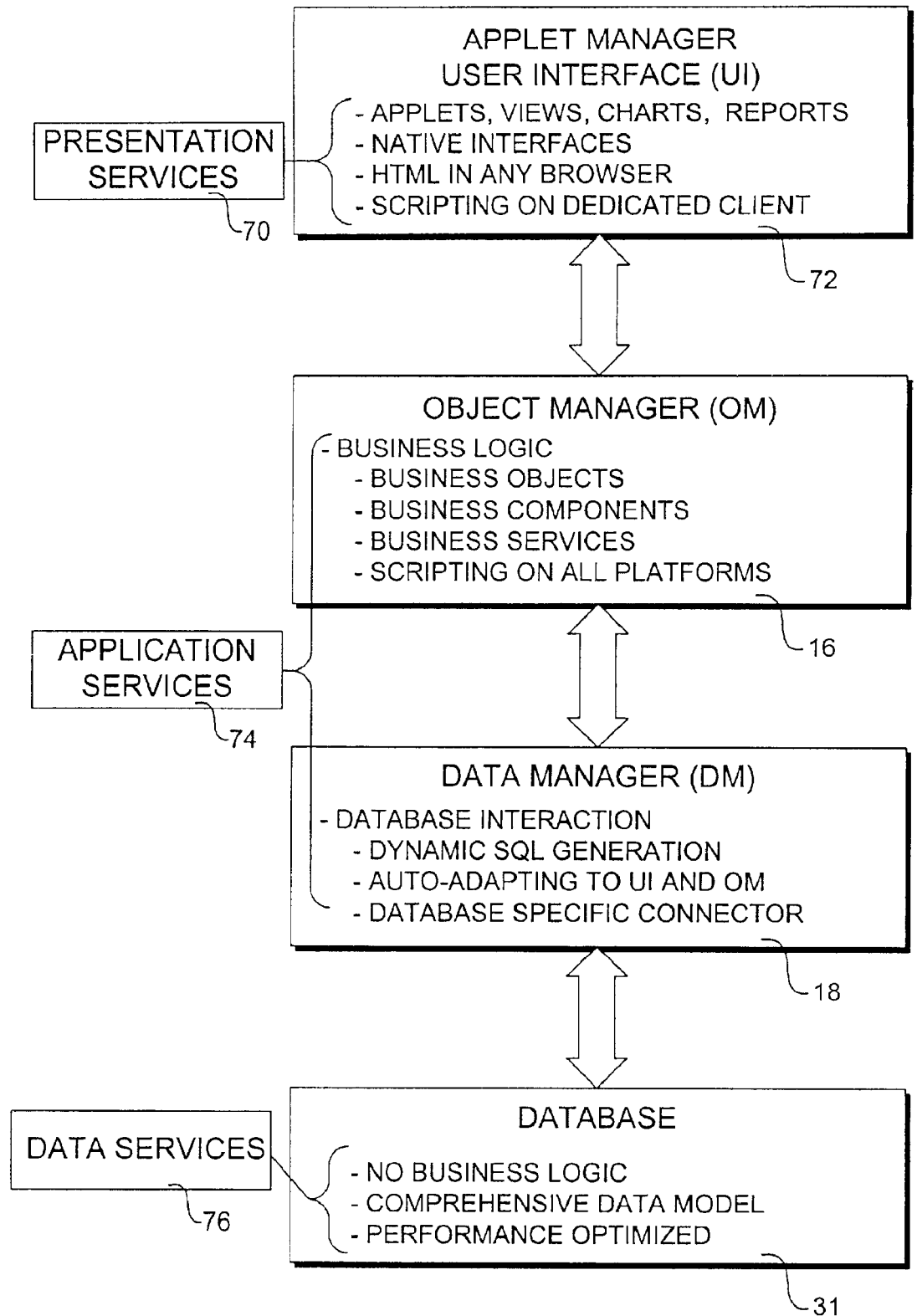
FIG. 3 is a block schematic diagram illustrating further details of the logical multi-layer architecture of FIG. 1.

FIG. 3 shows a block diagram illustrating another logical representation of a multi-layered architecture in which applications can be built in accordance with the teachings of the present invention. Again, the multi-layered architecture as illustrated in FIG. 3 provides the platform for various common services designed and configured to support the various operations provided by the invention. In one embodiment, these various services include a presentation services layer 70 corresponding to services provided by an applet manager and user interface 72, an application services layer 74 corresponding to services provided by object manager layer 16 and data manager layer 18, and a data services layer 76 corresponding to services provided by database 31.

In one embodiment, the presentation services 70 may be designed and configured to support various types of clients and may provide them with user interface applets, views, charts, and reports, etc. As described above, a large variety of clients may be supported including interactive web clients, mobile clients, and dedicated (connected) clients, etc.

In one embodiment, application services 74 may include business logic services and database interaction services. In one embodiment, business logic services provide the class and behaviors of business objects and business components implemented by the application services. In one embodiment, database interaction services may be designed and configured to take the user interface (UI) request for data from a business component and generate the appropriate database commands (e.g., SQL queries, etc.) to satisfy the request. For example, the data interaction services may be used to translate a call for data into DBMS-specific SQL statements.

Figure 4:
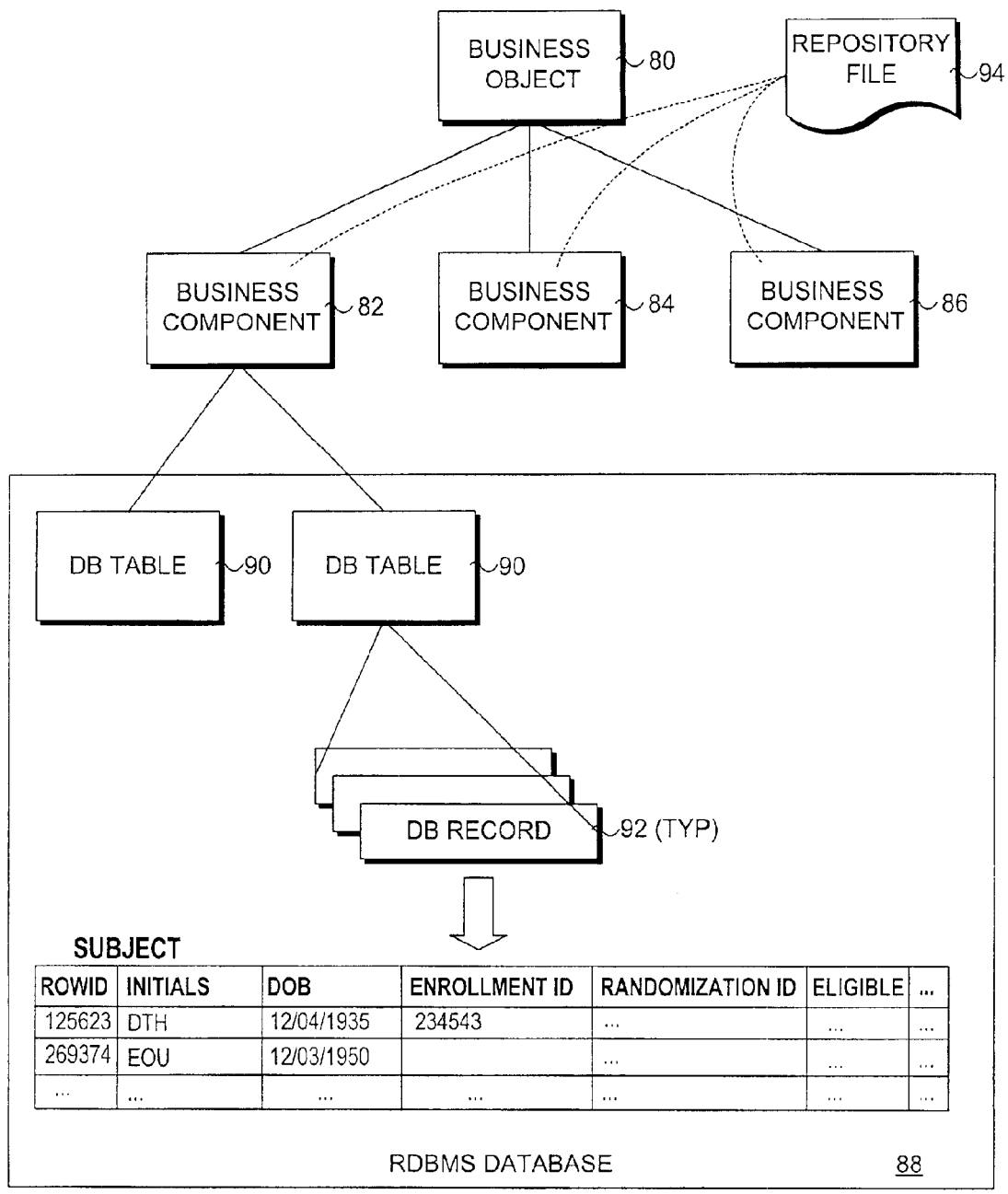
FIG. 4 is a block schematic diagram illustrating the hierarchical relationship between business objects, business components, and data storage in accordance with the multi-layer architecture of FIG. 3.

A multi-layer architecture illustrating the relationships between business objects, business components, and database tables is shown in FIG. 4. A business object 80 sitting at the top layer passes various database access request to business components 82, 84, and 86 to retrieve data pertaining to the business object from a database 88. For example, business object 80 may pertain to an opportunity object and business components 82, 84, and 86 are used to access data in database 68 pertaining to opportunities.

In one aspect, business components are objects that span data from one or more physical database tables and calculated values by referencing a base table and explicitly joining and linking other tables, including intersection tables, as depicted by tables 90, each of which include a plurality of records 92. As explained in further detail below, each business component contains information for mapping to various data stored in those tables. More specifically, these mappings are between a requested object, such as a subject, and information pertaining to that object that are stored in the database table(s) to which the business component corresponds. In one embodiment, database schema information stored in a repository file 94 is used by the business components in determining their table mappings.

Figure 5:
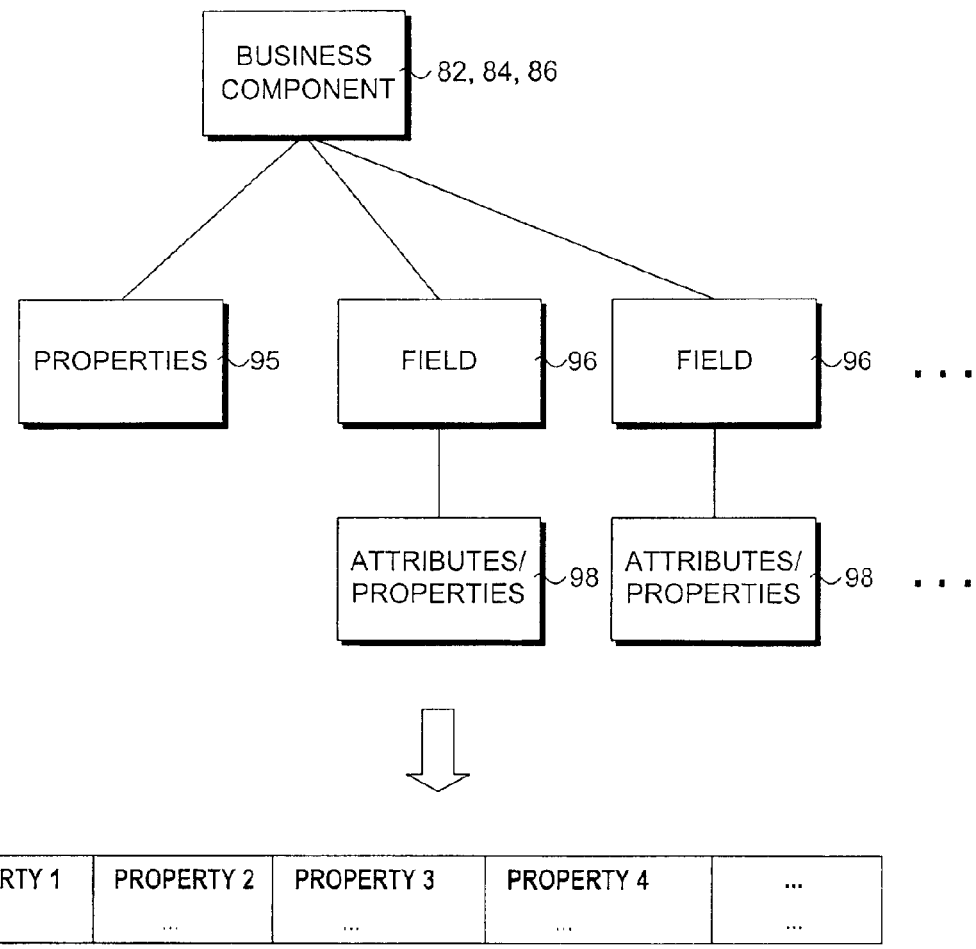
FIG. 5 is a block schematic diagram illustrating further details of a business component.

A block diagram of a logical structure of a business component in accordance with one embodiment of the present invention is shown in FIG. 5. Each business component (e.g., 82, 84, 86) may include a set of properties 95 that pertain to the respective business component (e.g., NAME, which specifies the logical name of the business component, TABLE NAME, which specifies the actual name of the underlying table, etc.). A business component also includes a set of fields 96, each of which may have a set of associated attributes or properties 98. For example, a field may include a NAME property that identifies the name of the field, a COLUMN NAME property that identifies the column of the underlying table to which the respective field is mapped, etc.

System Framework

FIG. 6 illustrates an exemplary system framework (i.e. infrastructure) 100 to support an interactive web client 32 and a mobile client 34 of FIG. 2 in accordance with one embodiment of the present invention. In addition to supporting these clients, the system framework is capable of meeting certain criteria, such as increasing the interactivity and performance of the web client and the mobile web client, and reducing the number of page refreshes for common actions. In a typical implementation, system framework 100 may include a set of browser side objects 102 that can be dynamically created on a client's browser (e.g., browser 34) to mimic corresponding objects managed by the object manager (OM) (OM-managed objects 104). In one embodiment, OM-managed objects 104 are defined by object classes built using an object-oriented programming language, such as C++or Java. Accordingly, objects and their corresponding classes are used interchangeably herein.

OM-managed objects 104 may include an object representing a view, in accordance with a CSSWEView class 106. A view is generally a display panel consisting of a particular arrangement of applets. Generally, one active view will be displayed at any given time. Another exemplary object managed by the OM can be an object representing an applet, as defined by a CSSWEApplet class 108. An applet is generally a visual application unit that appears on the screen as part of a view.

Other exemplary objects managed by the OM can include objects representing business components (defined by a CSSBusComp class 110), objects representing business objects (defined by a CSSBusObj class 112), and objects representing frames (defined by a CSSWEFrame class 114). A frame generally comprises a sub-component of a view and may comprise of one or more applets. In one embodiment, the business objects are designed as configurable software representations of the various business rules or concepts corresponding to those objects, such as accounts, contacts, etc, wherein the business components provide a layer of wrapping over tables that store data corresponding to the business objects, and the applets reference business components rather than the underlying tables to interface with the data.

In one embodiment, browser-side objects 102 are built using JavaScript to mirror the behavior of corresponding classes managed by the OM. An exemplary set of objects, as shown in FIG. 6, include a JSSBusObj class 116 object, a JSSBusComp class 118 object, JSSView class 120 object, and a JSSApplet applet class 122 object, each of which is configured to respectively mirror corresponding OM managed objects 104, including OBCSSBusObj class 112 objects, CSSBusComp class 110 objects, CSSWEView class 106 objects, and CSSWEApplet class 108 objects.

Figure 7A:
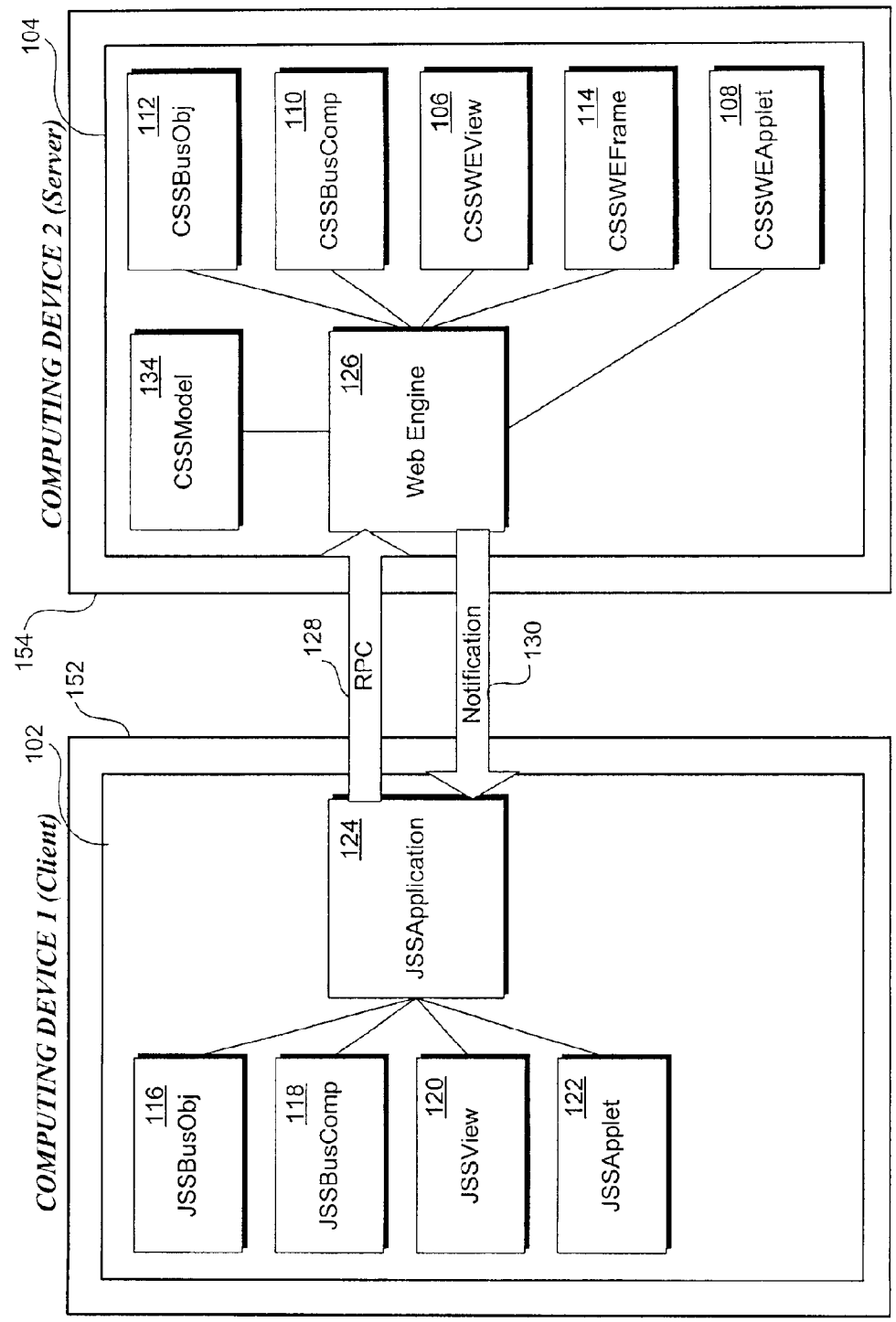
FIG. 7A is a block schematic diagram illustrating interaction between browser-side objects and object manager managed objects, wherein each set of objects are hosted by separate computing devices.
Figure 7B:
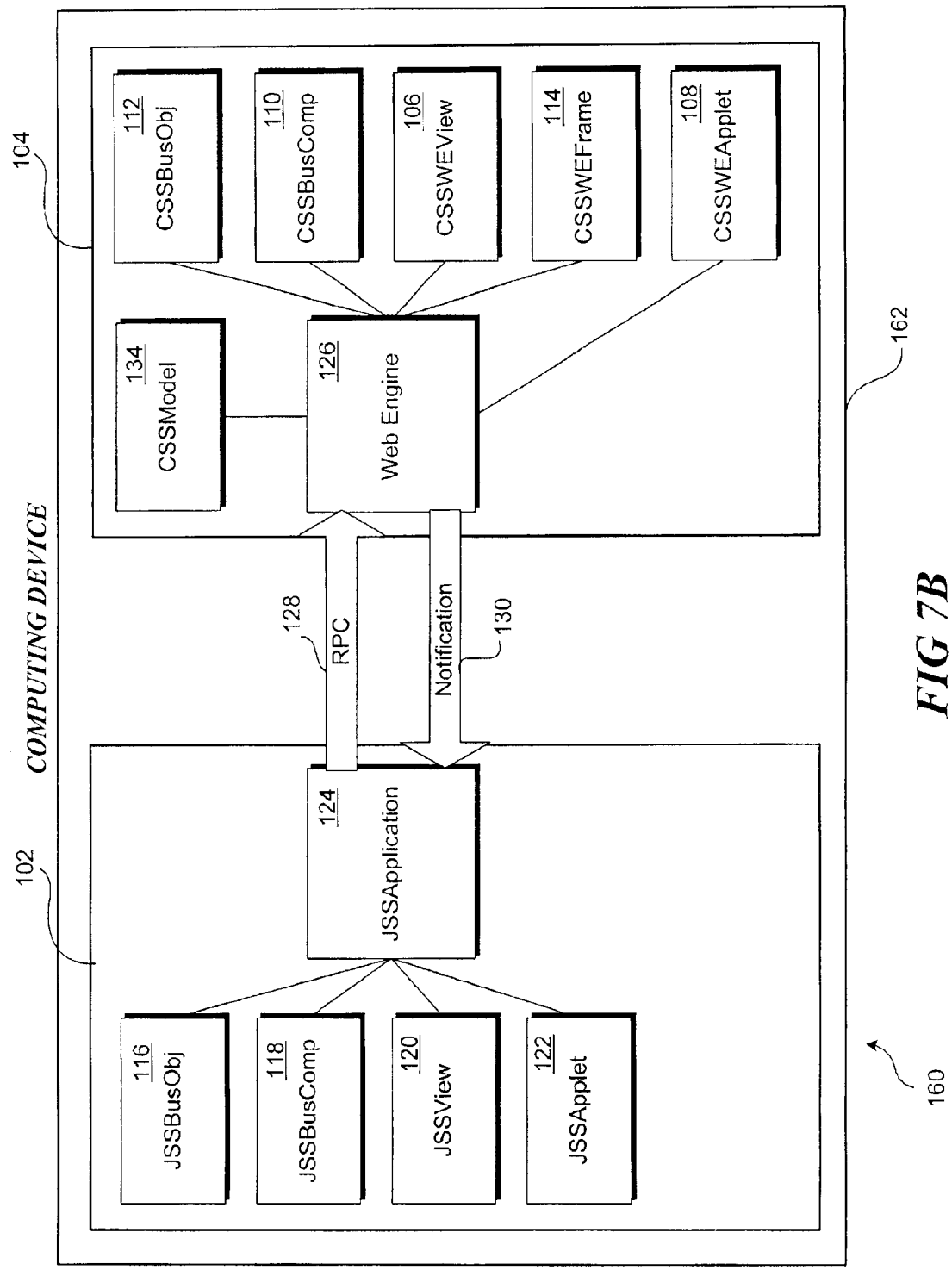
FIG. 7B is a block schematic diagram illustrating interaction between browser-side objects and object manager managed objects, wherein both sets of objects are hosted by the same computing device.

Browser-side objects 102 and OM-managed objects 104 can be configured to reside and operate on a single computing device or multiple computing devices. FIG. 7A illustrates an exemplary configuration 150 in which browser-side objects 102 and OM-managed objects 104 reside and operate on multiple computing devices, including a client 152 and a server 154. FIG. 7B illustrates an exemplary configuration 160 in which browser-side objects 102 and OM-managed objects 104 reside and operate on a single computing device 162.

Browser-side objects 102 further include an application object pertaining to a JSSApplication class 124 that typically exists throughout a user-session. The JSSApplication class should be initially loaded when an application invoking the class is loaded. The JSSApplication class objects generally perform a role similar to that of an OM-managed object corresponding to a CSSModel class 134. The CSSModel class generally defines a global session object that provides access to repository objects that are in use, the current business object instance in memory, the relationships between the current business object and the business components contained in it, and the user's global state information. CSSModel class 134 generally accesses a repository (e.g., repository file 28) to obtain this information. In general, a portion of the data stored in the repository will include a set of object definitions used to define an application or a suite of applications. However, the JSSApplication class 124 objects are generally scaled down to track one view, applets associated to the tracked view, one business object, and the business components that are in use in the view.

Unlike the JSSApplication class 124 objects, the objects corresponding to JSSView class 120, JSSApplet class 122, JSSBusObj class 116 and JSSBusComp class 118 are typically temporary or impermanent entities, and are generally replaced when a page refresh occurs. For example, a request to navigate to a new view may cause a new set of JSSView class 120, JSSApplet class 122, JSSBusObj class 116, and JSSBusComp class 118 objects to be created to run on the browser. Accordingly, browser-side objects 102 can be generally described as lightweight representations corresponding OM-managed objects 104.

In one embodiment, each browser-side object 102 typically includes a subset of the functionalities provided by its corresponding OM-managed object. For example, JSSView class 120 objects corresponding to CSSView class 106 objects generally represents a collection of applets. Additionally, JSSBusObj class 116 objects corresponding to CSSBusObj class 112 objects generally manage the various one-to-many relationships between active business components so that correct relationships are employed when these active business components are populated via queries. JSSBusObj class 116 objects generally exist on the browser for the life of a current view, and should be kept in synchronization with its corresponding CSSBusObj class 112 object. Returning to FIG. 6, browser-side objects 102 are generally synchronized with corresponding OM-managed objects 104 using a remote procedure call (RPC) mechanism 128 and a notification mechanism 130.

In addition to OM-managed object 104, the object manager also includes a web engine 126. The web engine is used to generate HTML-based data corresponding to OM-managed objects 104, and to also interface with JSSApplication class 124 objects via RPC mechanism 128 and notification mechanism 130. In one embodiment, when the browser submits a request to navigate to a new view to web engine 126, the web engine first send a response containing an appropriate view layout that is devoid of data. Then the web engine sends a response containing a string of data to populate the view.

The JSSApplication class 124 objects generally manage communications flowing into and out from objects on the browser. In one embodiment, a method invoked on an object on the browser would typically be directed to the JSSApplication class object if the invoked method should be retargeted to an OM-managed object 104. The JSSApplication class object would generally use RPC mechanism 128 to route the invoked method through web engine 126 to an appropriate OM-managed object 104. Typically, web engine 126 will be employed to send return notifications and data from OM-managed objects 104 on the browser. Accordingly, web engine 126 will generally use notification mechanism 130 to route notifications and data through JSSApplication class 124 objects to appropriate browser-side objects 102 specified in the notifications.

The browser-side objects generally use remote procedure calls supported by RPC mechanism 128 to invoke methods on the OM-managed objects. These remote procedure calls are generally packaged as HTMP requests. Responses from OM-managed objects 104 are packaged as HTTP responses containing notifications and associated status information and data. In one embodiment, remote procedure calls are made with blocking enabled to ensure synchronization between browser-side objects 102 and OM-managed objects 104. With blocking enabled, control would typically not be passed back to the calling code until the called remote procedure finishes executing.

Further details of the RPC mechanism and other details pertaining to the system framework are disclosed in co-pending patent application Ser. No. 09/969,856, filed on Sep. 29, 2001 and entitled "METHOD, APPARATUS, AND SYSTEM FOR IMPLEMENTING A FRAMEWORK TO SUPPORT A WEBBASED APPLICATION," the specification and drawings of which are incorporated by reference herein.

Figure 8:
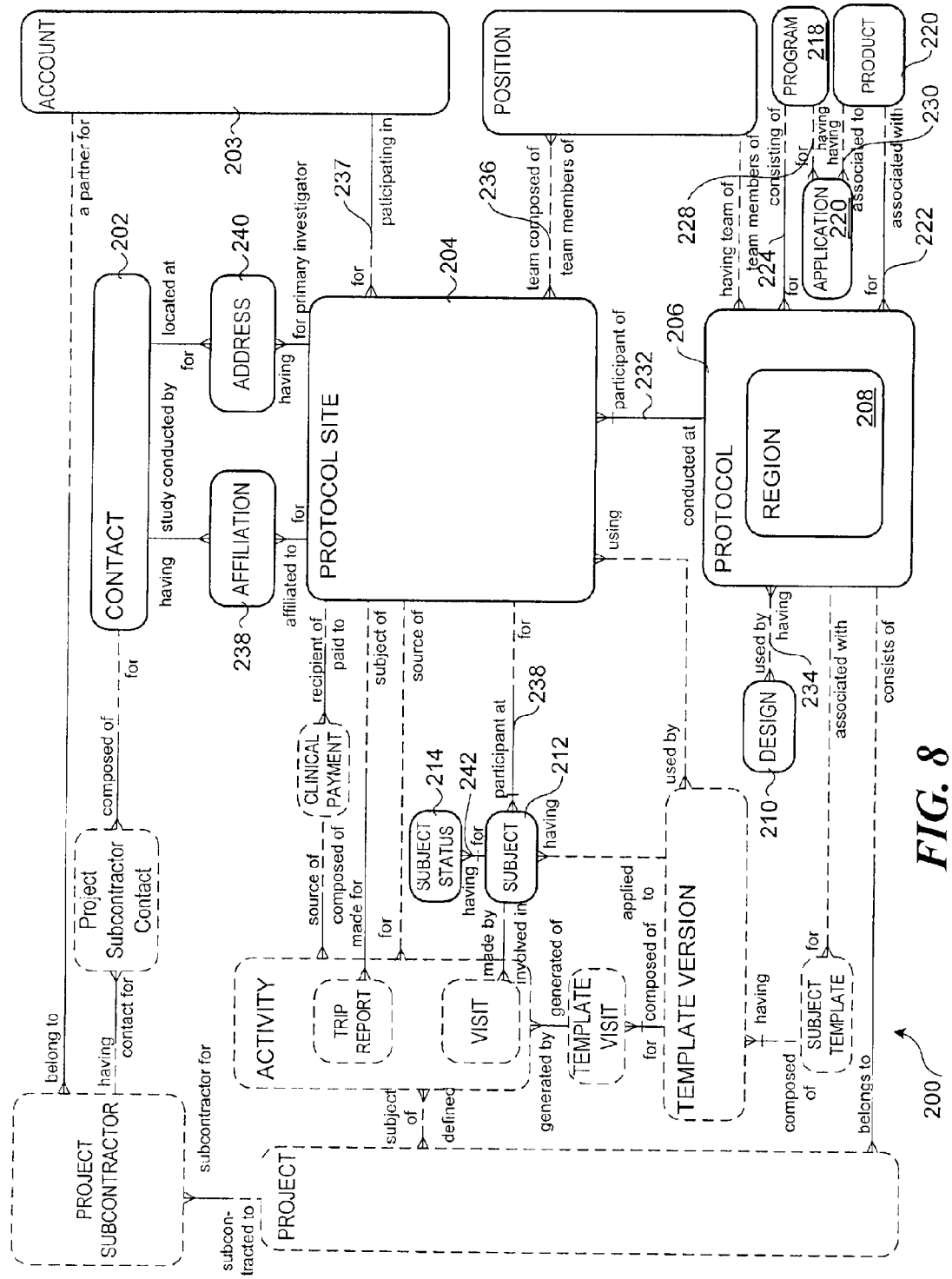
FIG. 8 is an entity-relationship diagram corresponding to an exemplary data model under which data storage aspects of the invention may be implemented.

An Entity Relation (ER) Diagram 200 (based on Oracle's nomenclature) corresponding to an exemplary logical data model for implementing data storage aspects of the invention is shown in FIG. 8. In general, ER Diagram 200 pertains to an eClinical application system that includes various aspects pertaining to the invention and other aspects that are outside the scope of the invention, such as billing activities, visits, trip reports, etc. Accordingly, entities pertaining to these aspects, while shown on the diagram, will not be discussed in further detail. Furthermore, the various attributes for each entity are not shown for clarity. Generally, the particular set of attributes used for each entity will depend on the particular needs of the implementation.

Entities pertaining to particular aspects of the invention include a contact entity 202, an account entity 203, a protocol site entity 204, a super-type protocol entity 206 that includes a sub-type region entity 208, a design entity 210, subject entity 212, a subject status entity 214, a position entity 216, a program entity 218, and a product entity 220. As defined by a many-to-one relationship 222, each protocol is associated with one product, while a product may have several protocols. As defined by a many-to-one relationship 224, each program consists of multiple protocols, while an application intersection table 226 and corresponding many-to-one relationships 228 and 230 relate each program to one or more products.

A many-to-one relationship 232 provides that each protocol requires at least one (and usually multiple) protocol sites to participate in that protocol. Each protocol also may be based on one or more designs, while each design may be used by zero or more protocols, as indicated by a many-to-many relationship 234 (corresponding intersection table not shown). Each protocol site includes a plurality of site personnel corresponding to a site team, headed by a principal investigator. The positions of the team members are defined by position entity 216, wherein a given team may have zero or more members occupying each position, and a person having a given position may be a team member at more than one site, as indicated by a many-to-many relationship 236 (corresponding intersection table not shown). For example, a principal investigator can participate in multiple protocols conducted at the same or different protocol sites. Each protocol site is also associated with an account, which are institutions such as hospitals and clinics where the studies are conducted. As provided by a many-to-one relationship 237, an account can host multiple protocol sites.

Contact details for the various site personnel are stored in a table corresponding to contact entity 202. An affiliation intersection entity 238 enables each contact to be affiliate with one or more protocol sites, while an address intersection entity 240 is used to store the addresses for the primary investigators for each protocol site.

Each protocol involves the evaluation of the drug on a plurality of subjects. Each of these subjects will participate (be screened or enrolled) at a particular protocol site, as indicated by a many-to-one relationship 238. Each subject may also have one or more statuses, as provided by a many-to-one relationship 242. As a subject's status is changed (e.g., from screened to enrolled, from enrolled to completed, etc.), a timestamp is stored in the table corresponding to subject status 214 so as to provide a historical records of a subjects statuses over the course of a clinical trial. Furthermore, a given subject may participate in multiple protocols over time. However, that subject is thought of as a different subject for each different protocol.

Typical Usage Scenario

The following scenario pertains to an example of a workflow performed by sponsor and clinical site personnel. Depending on the particular business requirements, the actual workflow may differ somewhat from this example. In the scenario, the clinical director and/or study managers, working for a sponsor such as a clinical research organization, pharmaceutical, biotech or medical device company, have administrative responsibilities, including: 1) setting up a new treatment study program; 2) creating one or more protocols designed to assess the safety of the tested compound (e.g., drug) or treatment modality; and 3) setting up the geographic regions (as applicable) where the protocols are to be carried out.

Once parameters pertaining to the program, protocol, and (if applicable) regions are defined, CRAs (typically) enter the following data into the system: 1) sites where the protocols are to be carried out; 2) accounts where the studies are to be conducted; 3) contacts, which include site personnel such as investigators, site coordinators, and nurse practitioners who carry out the protocols. The CRAs are also involved with screening and enrolling subjects, performing rescreening, if necessary, and updating the status of each subject in the event of a status change. As described in further detail below, the task of entering subject data pertaining to the screening and enrollment of subjects may also be performed by the site personnel using the portal web site provided by the system.

At various times after the subjects have been enrolled in the trial, the clinical director, study manager, or CRAs are enabled to review the progress of the trial using the charting features provided by the present invention. Two informative metrics provided by these charting features include subject status and enrollment rate. These may be plotted for an individual site, sites within a region, and sites across an entire protocol.

As described below, an exemplary set of user interface views are discussed with reference to representation of those views in the drawing Figures. It is noted that some of the views are shown to include edit controls that are not discussed herein. These edit controls concern aspects of the eClinical system that are beyond the scope of the present invention, and, accordingly, no further details will be provided beyond that shown in the drawing Figures.

Figure 9:
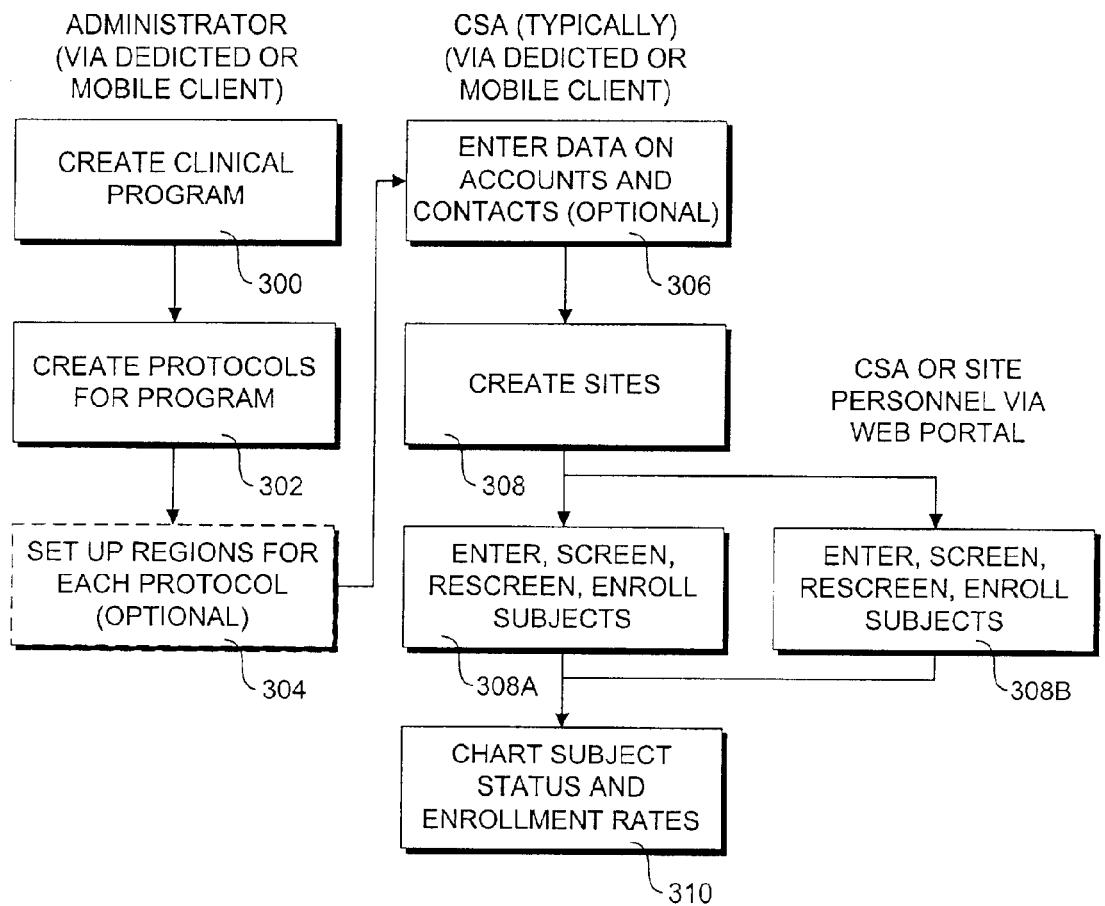
FIG. 9 is a flowchart illustrating a workflow encountered during a typical usage scenario.
Figure 10:
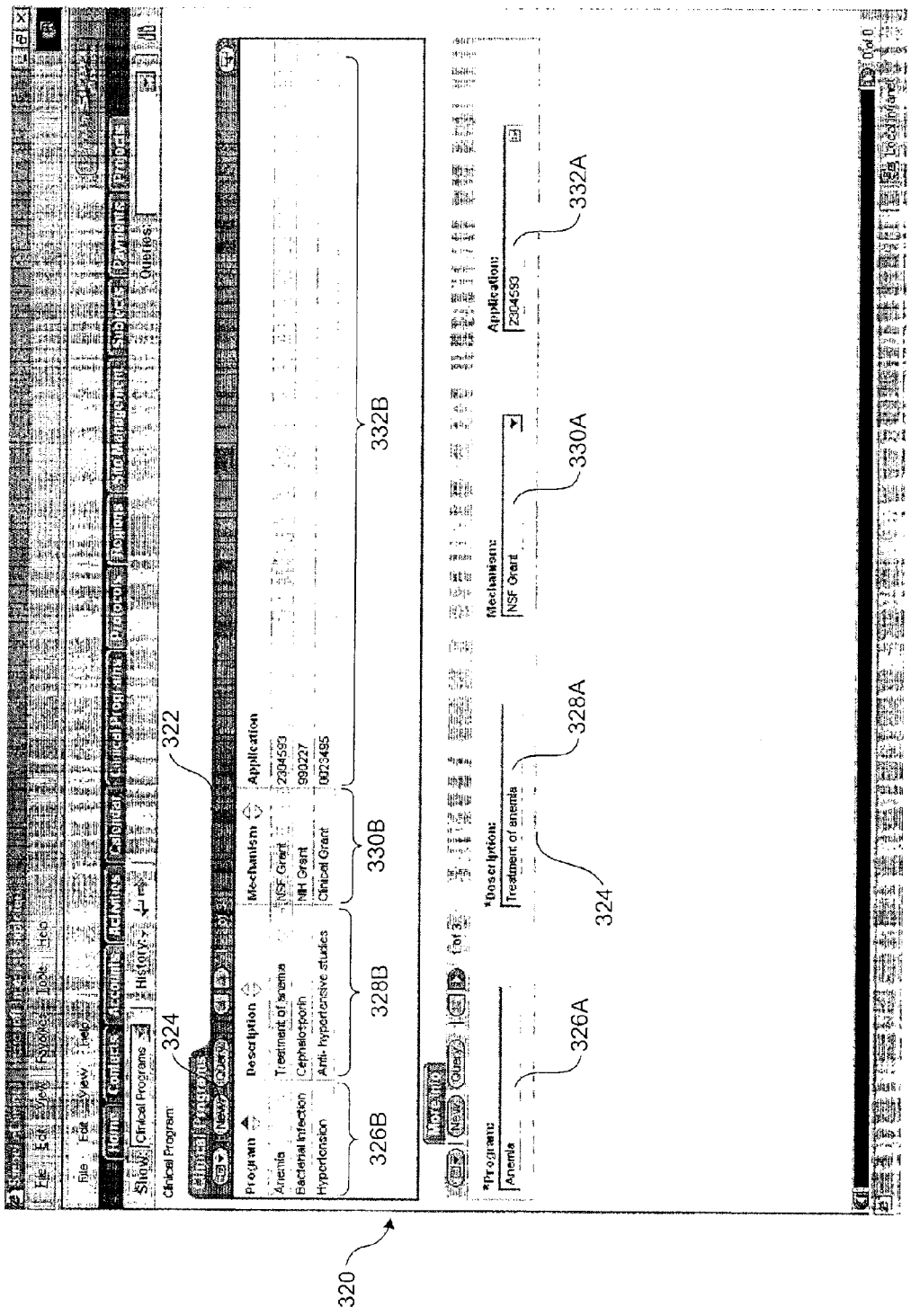
FIG. 10 is a representation of a clinical program view that enables clinical trial program parameters to be entered by a user of an eClinical computer application in accordance with the invention.

With reference to FIG. 9, a typical usage scenario begins in a block 300, in which an administrator defines parameters for a clinical program. This will typically be done using either a dedicated client 36 or a mobile client 34. If a mobile client is used, a database synchronization will need to be performed to propagate any entered data to enterprise database 31. A representation of an exemplary View 320 for performing this task is presented in FIG. 10. View 320 includes a clinical program header applet 322 and a clinical program details applet 322.

View 320 and the other user interface views discussed below are built based on object class definitions corresponding to the architectures and system framework discussed above. For example, specifications defining the look and functionality of the various applets are defined by JSSApplet class 122 and any applicable subclass dependent thereon. Furthermore, each of clinical header summary applet 322 and clinical program detail applet 324 correspond to user interface layer 14 in FIG. 1 and presentation services 70 in FIG. 3. In the case of dedicated client 36, the OM-managed components 104 and the browser-side components both reside on the same computing device (e.g., desktop computer 40). As discussed above, in one embodiment the browser side objects are written in Javascript, and enable users to enter data (herein after referred to as clinical trial parameters) into interactive edit controls on clinical program detail applet 324, including a program edit box 326A, a description edit box 328A, a mechanism dropdown control 330A, and an application multi-value dialog picklist control 332A, each corresponding to respective fields in clinical programs summary applet 322, including a program field 326B, a description field 328B, a mechanism field 330B, and an application field 332B. It is noted that each of the fields in the clinical program summary applet may also be configured as editable fields in accordance with known web-based user interface techniques.

Activation of a "New" button 334 on clinical program summary applet 322 or a "New" button 336 on clinical program detail applet 324 creates a new blank row in clinical program summary applet 322 and clears the edit boxes and dropdown control in program detail applet 324. The name of the clinical program may then be entered into program edit box 326A, while a description of the program is entered into description edit box 328A. A mechanism, corresponding to a partner associated with the clinical program, such as NSF (National Science Foundation) and NIH (National Institute of Health) grants, is selected from dropdown control 330B. Additional, information pertaining to the application submitted to support the clinical trial, such as a number assigned to the application by a regulatory agency, may be selected via application multi-value dialog picklist control 332A.

Each of edit controls 326A, 328A, 330A, and 332A is mapped to a respective table column in enterprise database 31 via business logic contained in one or more corresponding business components managed by object manager 16 and through database interaction services provided by data manager 18. For example, in one embodiment each of program field 326B, description field 328B, mechanism field 330B, and application field 332B is mapped to a PROGRAM table corresponding to program entity 218 in the data model of FIG. 8. Upon activation of a save command (not shown), current data corresponding to the edit controls are posted to enterprise database 31.

Figure 11:
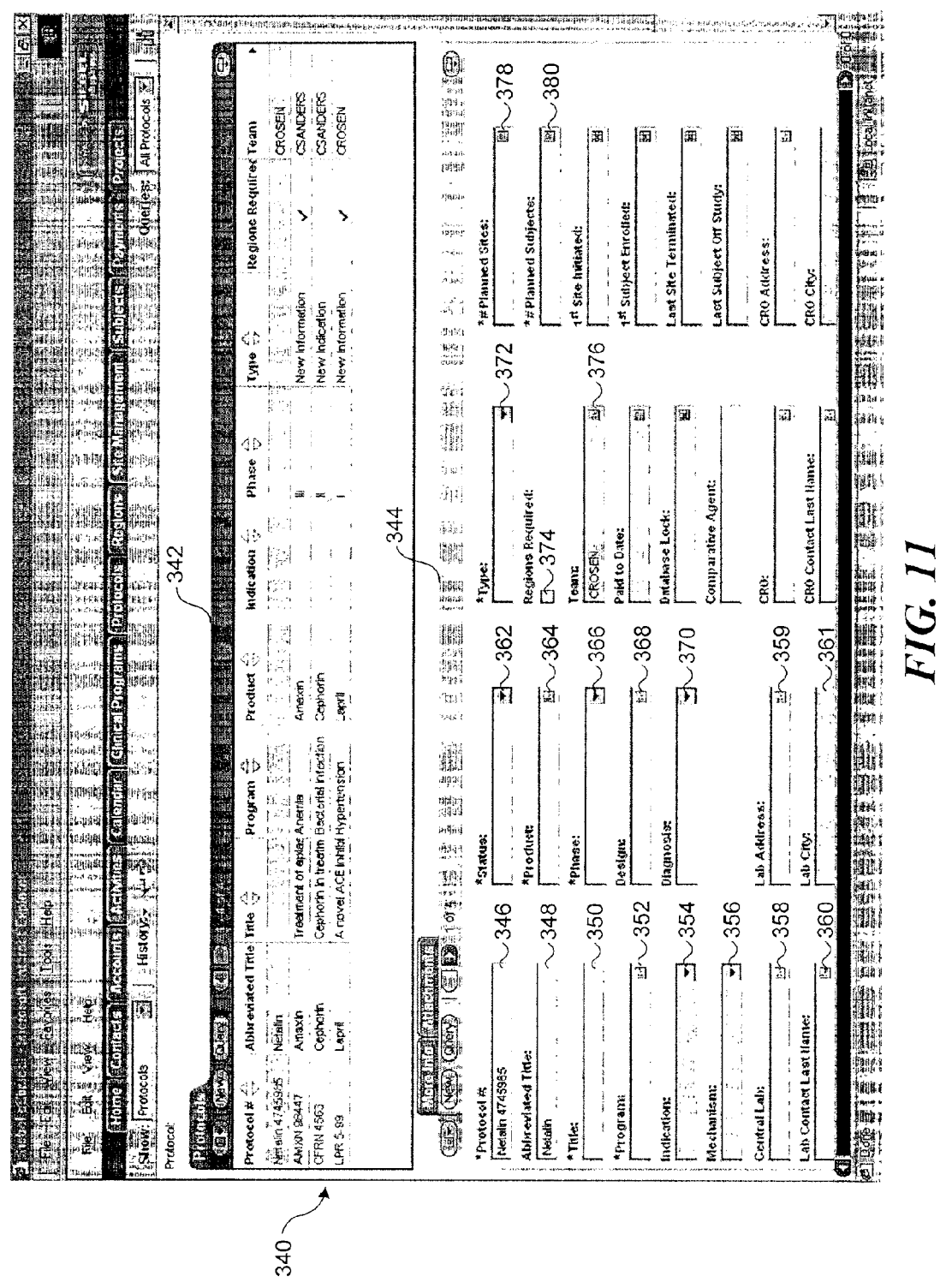

Returning to the flowchart of FIG. 9, once parameters defining a clinical program have been provided, the administrator creates one or more protocols for the program. In general, multiple protocols and multiple versions of a protocol can be associated with a program. A representation of a view 340 to enable protocol information to be entered and stored in enterprise database 31 is shown in FIG. 11.

View 340 includes a protocol summary applet 342 and a protocol detail applet 344. In a manner similar to view 320 discussed above, the protocol summary applet includes various fields, wherein data is displayed on a row-wise basis, while the protocol detail applet includes a plurality of edit and dropdown controls to enable parameters to be defined on a field-wise basis for a given protocol. The field include required fields, as indicated by an "*" adjacent the field name, and optional fields. The corresponding field edit controls include a protocol # edit box 346 in which the number assigned to the protocol is entered, an abbreviated title edit box 348 in which an abbreviated title for the protocol may be entered and a title edit box 350 in which the protocol's full title is entered. The name of the program under which the protocol is to be performed may be selected from a list of previously entered programs that are retrieved from enterprise database 31 via activate of a multi-value dialog picklist control 352. An indication dropdown control 354 and a mechanism dropdown control 356 are automatically populated with an appropriate indication and mechanism upon selection of a product and program, respectively.

The name of the central laboratory conducting analysis of samples from the trial (as applicable) may be entered in a central lab edit box 358, while the last name of a contact person associated with the central lab may be entered in an edit box 360. A corresponding lab address and lab city may be respectively entered via edit controls 359 and 361.

The protocol status, such as planned, in progress, or completed, is entered in a status edit box 362, while a product that has been previously associated with the clinical program can be selected from a list via activation of a query control 364 that will query enterprise database 31 to return a list of valid products based on the program name in the program edit box. The phase for the protocol, typically Phase I, Phase II or Phase III, may be selected from a dropdown control 366. A design containing information about the type of study to which the protocol corresponds may be selected for a list of applicable designs retrieved from enterprise database 31 in response to the activation of a query control 368. A diagnosis may be selected via a dropdown control 370.

A type parameter corresponding to the purpose of the protocol may be selected via a dropdown control 372. If regions are required, a check may be placed in a checkbox 374. By checking the checkbox, the administrator indicates the site for the protocol must belong to a region, and that sites cannot be created directly under the protocol without creating regions first and then associating the sites with the regions. The names of those who need access to the protocol, such as the study manager and other who monitor the clinical trial may be entered in a multi-value dialog picklist control 376. The number of sites planned for the protocol may be entered via a control 378, while the number of subject planned for the protocol may be entered via a control 380.

Figure 12:
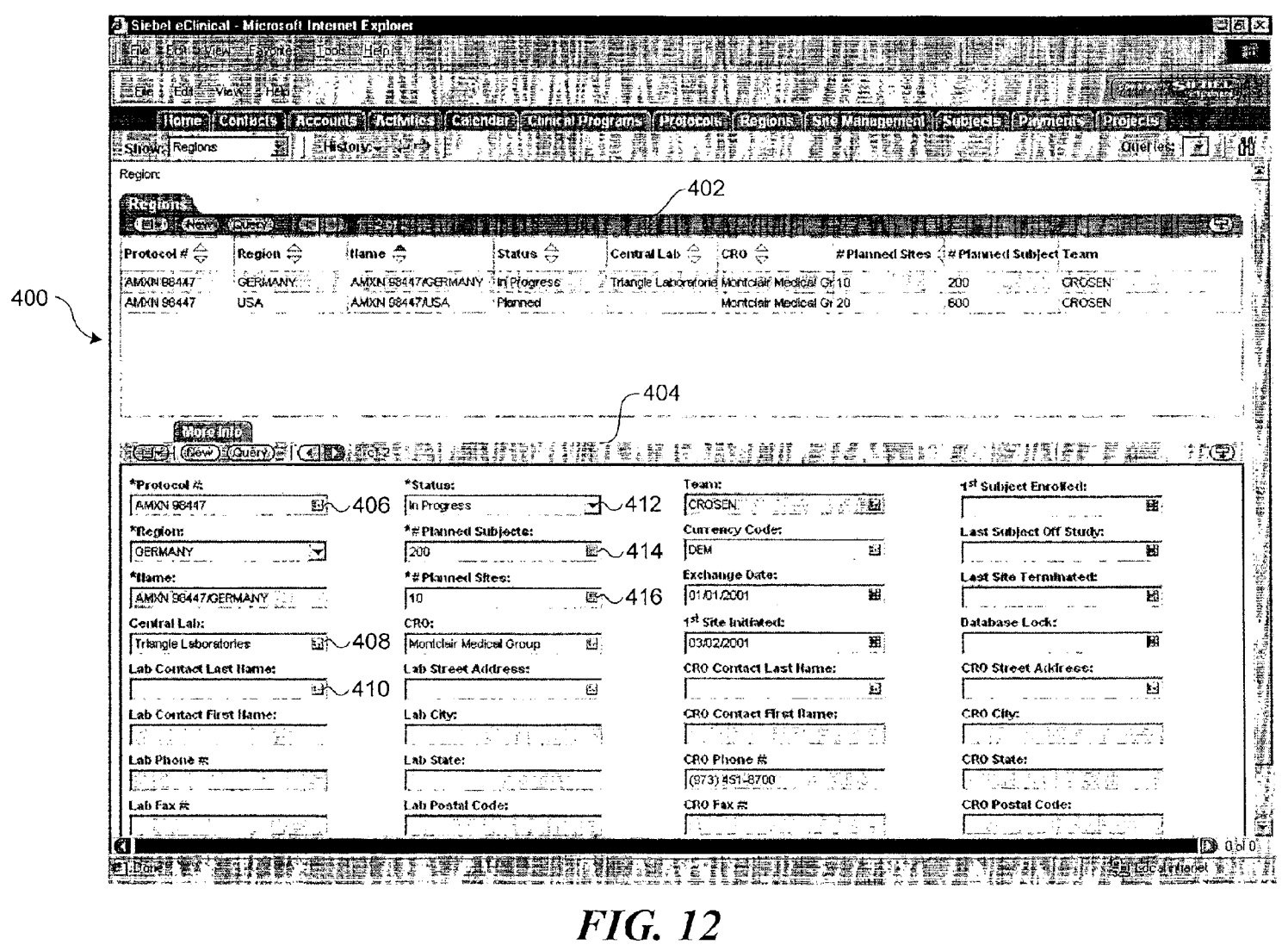

Once parameters for one or more protocols have been defined, regions may be set up for each protocol, if desired, as provided by a block 304 in FIG. 9. This comprises filling out appropriate information in a view 400, as shown in FIG. 12. UI page 400 includes a region summary applet 402 and a region detail applet 404. The user may select a protocol number via a multi-value dialog picklist control 406, whereby the protocol numbers presented in the multi-value dialog picklist only include protocols that were defined to require regions. The region may be selected from a dropdown control 408, while the name of the region is automatically generated in a text box 410 comprising a combination of the protocol number and the region. An applicable status is selected from a dropdown control 412. The planned number of subjects and planned number of sites may be entered via edit control 414 and 416, respectively.

At this point, the work shifts to a CRA, as shown in FIG. 9, wherein account and contact data may be entered via corresponding views (not shown) in a block 306. An account is the institution from which clinical trials are managed. Typically, it is the facility where the investigators conduct the trials. More than one site can be associated with an account, and one account can be carrying out multiple protocols. IRBs (institutional review boards), center labs, CROs (clinical research organizations), and other subcontractors may also be tracked as accounts. Contacts is the term used for personnel working at clinical sites. This includes the investigators, typically medical professionals who are also researchers, and site coordinators, who may be the practicing nurses administering the treatment plan according to the clinical protocol. Typically, bulk loading data corresponding to accounts and contacts is performed by an IT administrator, but end users may add and modify these records as needed.

Figure 13:
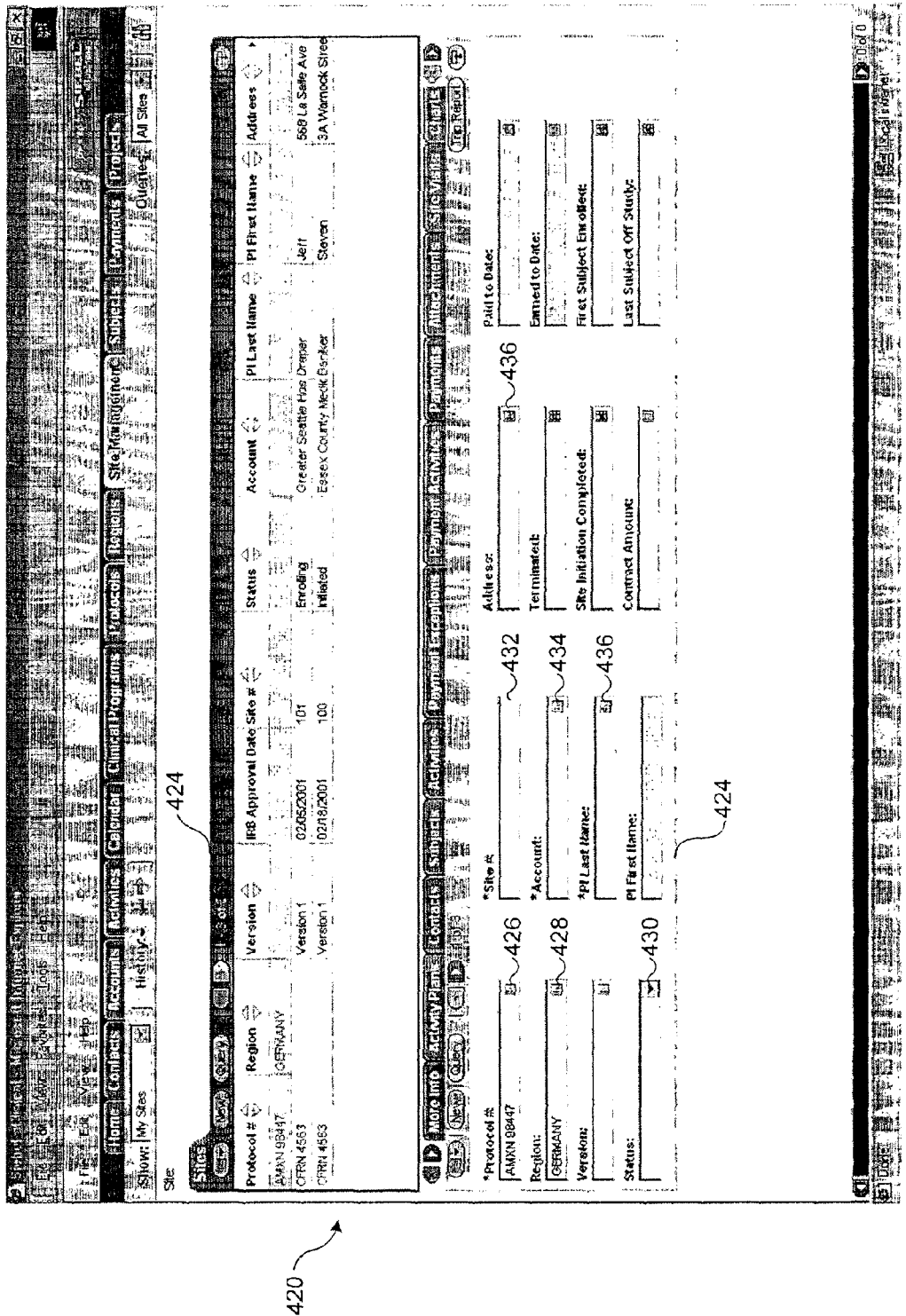
FIG. 13 is a site view that enables various clinical trial site parameters to be defined by users of the eClinical application.

Next, the CRA enters parameters for creating sites in a block 308. The site is the group at an account, headed by a principal investigator, who carries out a particular protocol. In one embodiment, a separate site record must exist for each unique combination of protocol, account, and principal investigator. A site view 420 that enables various site information to be entered in a site summary applet list 422 and a site detail applet form 424 is shown in FIG. 13. The site details may be entered on the site detail applet form via various edit controls, including a protocol number multi-value dialog picklist control 426 that is activated to generate a list of existing protocols from which the protocol can be selected. Similarly, an appropriate region (if applicable) may be selected via a region multi-value dialog picklist control 428. The status for the site may be selected via a dropdown control 430, while a site number is entered an edit box 432.

Each site is required to have at least one account, which can be selected via activation of a picklist dialog control 434. The last name of the principal investigator is selected via a picklist dialog control 436. If an account has already been specified for the site, activation of an affiliated contacts control in the pick contacts dialog box (not shown) will limit the list to only those contacts affiliated with the account. The address for the principal investigator may then be selected from among any addresses corresponding to the principal investigator that have been previously entered via activation of a picklist dialog control 438.

Once parameters pertaining to the sites have been defined (and stored in enterprise database 31), site personnel may screen, re-screen, and enroll subjects via the web portal (as provided by a block 308B). The same information maybe entered by CRAs using a dedicated or mobile client (as provided by a block 308 A) In order to access the web portal, the site user will need to be authorized to use the site portal and be provided with a user ID and password. The user will enter an appropriate URL for the site, and upon reaching a login page (not shown) the user will enter his or her user ID and password. The user ID and password combination will be authenticated (typically through data stored in the enterprise database or through a third party authentication tool), and a database connection will be established. In one embodiment, the site personnel user is uniquely identified by a combination of contact information (correlated to a login identity) as well as the position/responsibility of a proxy user the login is associated with. In response to establishing this unique identity, the system will generate a "home" view based on data specific to the user through query of the enterprise database to fill various data fields in the view.

Figure 14:
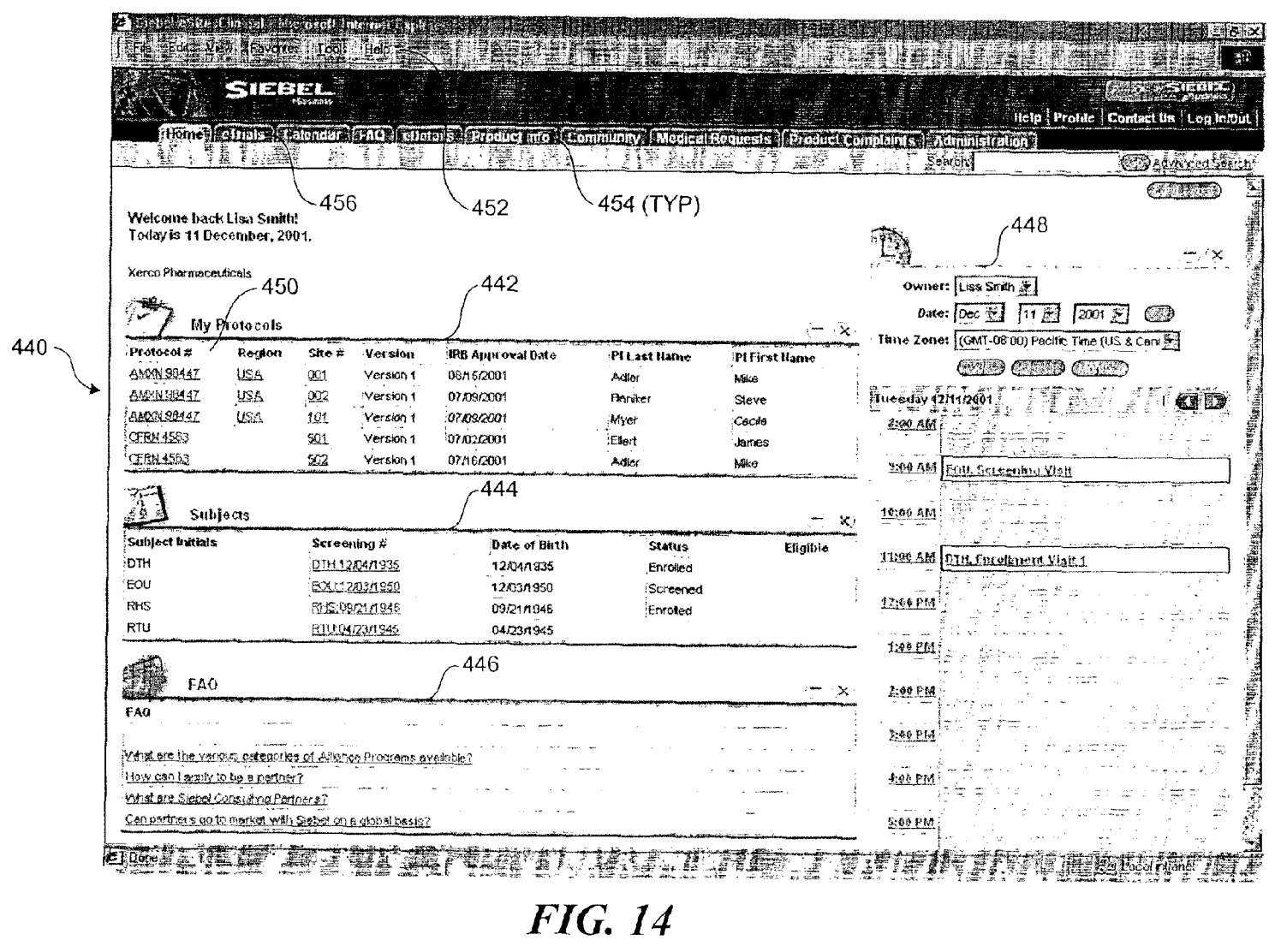

For example, a home view 440 corresponding to a "Lisa Smith" is shown in FIG. 14. Home view 440 includes a "My Protocols" applet list 442, a subjects applet list 444, a FAQ (frequently asked question) applet 446, and a calendar applet 448. Various field underlined field values comprise hyperlinks to the data corresponding to the field. For example, activation of any of the protocol number hyperlinks in a protocol # column 450 will cause a view corresponding to the protocol to be generated and presented on the user's browser. Home view 440 also includes a pull down menu 452 and a plurality of view tabs 454.

Figure 15:
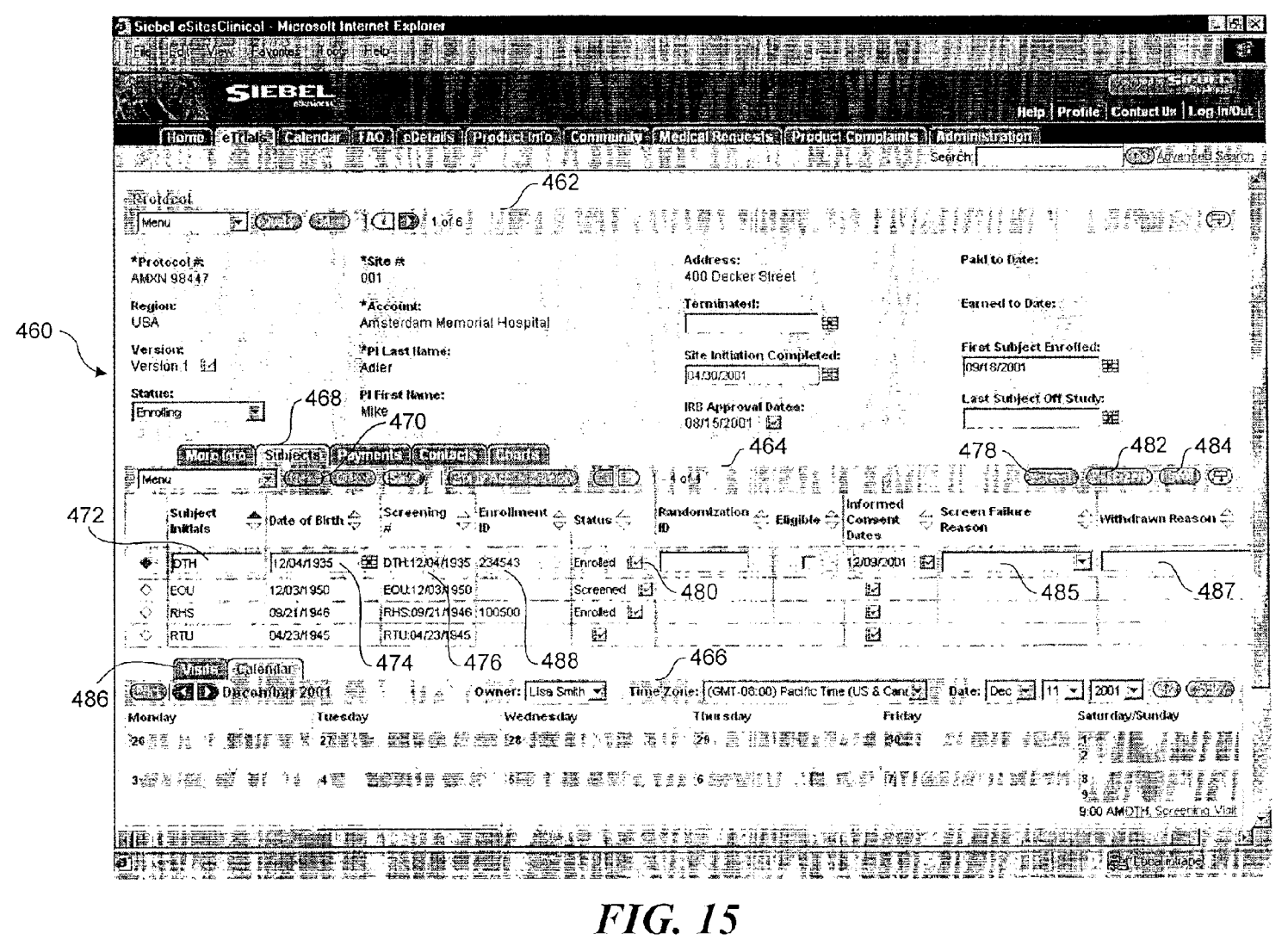

Activation of a "eTrials" view tab 456 causes an eTrials view 460 to be dynamically built, with corresponding framework and data sent to interactive web client 32 and rendered on browser 34, as shown in FIG. 15. eTrials view 460 includes a protocol applet form 462, a subjects applet form 464, and a calendar applet form 466. Subject data is specific to a protocol and a site. Upon selecting a protocol and site, and selecting a subjects tab 468 (if not initially selected), subject applet form 464 will be populated with data pertaining to subjects previously screen, re-screened, or enrolled.

To add a new subject, the user activates a "New" button 470, which causes a new blank row to appear in the subject applet form. The user then enters the new subject's initials in an edit box 472 and the subject's date of birth in an edit box 474. A non-editable text box 476 will then be automatically filled with a screening number upon saving the record. In one embodiment, the screening number comprises a combination of the subject's initials concatenated with the subject's date of birth.

The status of a subject can either be "screened," "re-screened," "screen failure," "enrolled," "completed," or "early terminated." Optionally, additional subject statuses may be configured, such as randomized, deceased, etc. To assign the "screened" status to a given subject, the user may either activate a "Screen" button 478, or activate a dialog picklist control 480 and select it from the list generated in the corresponding dialog. Similarly, a "re-screened" status can be assigned via selection of a "Re-screen" button 482 or the dialog pick list control, while a status of "enrolled" can be assigned via selection of an "Enroll" button 484 or the dialog pick list control. If a subject has failed a screening or has been withdrawn, reasons for such may be respectively selected via a dropdown control 485 and an edit box 487.

In order to be enrolled, the subject must have signed an informed consent form, the date of the signing of which must be entered. In one embodiment, this information is entered in a "Visits" form that is activated via a "Visits" tab 486. Upon activation of "Enroll" button 484 user needs to enter an enrollment ID in the Enrollment ID text box 488 and enrollment date in the Enrollment Date text box. Upon activation of any of "Screen" button 478, "Re-screen" button 482 and "Enroll" button 484, the various data fields corresponding to the subject record are checked for validity, and the corresponding data written to enterprise database 31. The actual handling of the data from interactive web client 32 to enterprise database 31 proceeds as follows. At a top (user interface) level, the applet used to enter the records automatically handles the user-interface aspects of the form or list corresponding to the applet. Upon a save-type event (e.g., activation of "Enroll" button 484), a remote procedure call is made to begin a process that passes the data entered on the applet form or list from the JSSApplet class 122 corresponding to the applet to a corresponding CSSWEApplet 108 on one of application servers 54 the interaction between an appropriate JSSApplication class 124 object and web engine 126. Typically, the data will be sent via HTTP over TCP/IP.

Once at the application server, appropriate interaction will take place between object manager 16C and data manager 18C to store the data in enterprise database 31. A portion of the business logic to handle this process will be defined in a business component corresponding a CSSBusComp class 110 object that is designed to interface with the CSSWE-Applet class object corresponding to the form.

The web portal provides several advantages over the prior art. Due to the design of the architecture and system framework, the web-based views provided by the portal are substantially identical with the views provided by a corresponding eClinical application that is run on dedicated client 36 or mobile client 34. Furthermore, the subject data can be retrieved, updated, added to, and stored from any physical location that provides access to an Internet connection. Importantly, as any data are entered or updated, those changes are immediately reflected in enterprise database 31 as they occur. As a result, the data in enterprise database 31 always reflects "real-time" data corresponding to any ongoing clinical trails.

In accordance with the foregoing "real-time" data storage aspects of the invention, clinical trial administrative personnel, such as CRAs are enabled to generate various charts that reflect real-time subject status and enrollment data, as provided by a block 310. Through an intuitive set of user interface options, users can easily select to have charts generated to reflect status and enrollment data aggregated across various summary levels, including by site, by region (where applicable), and across an entire protocol.

Figure 16:
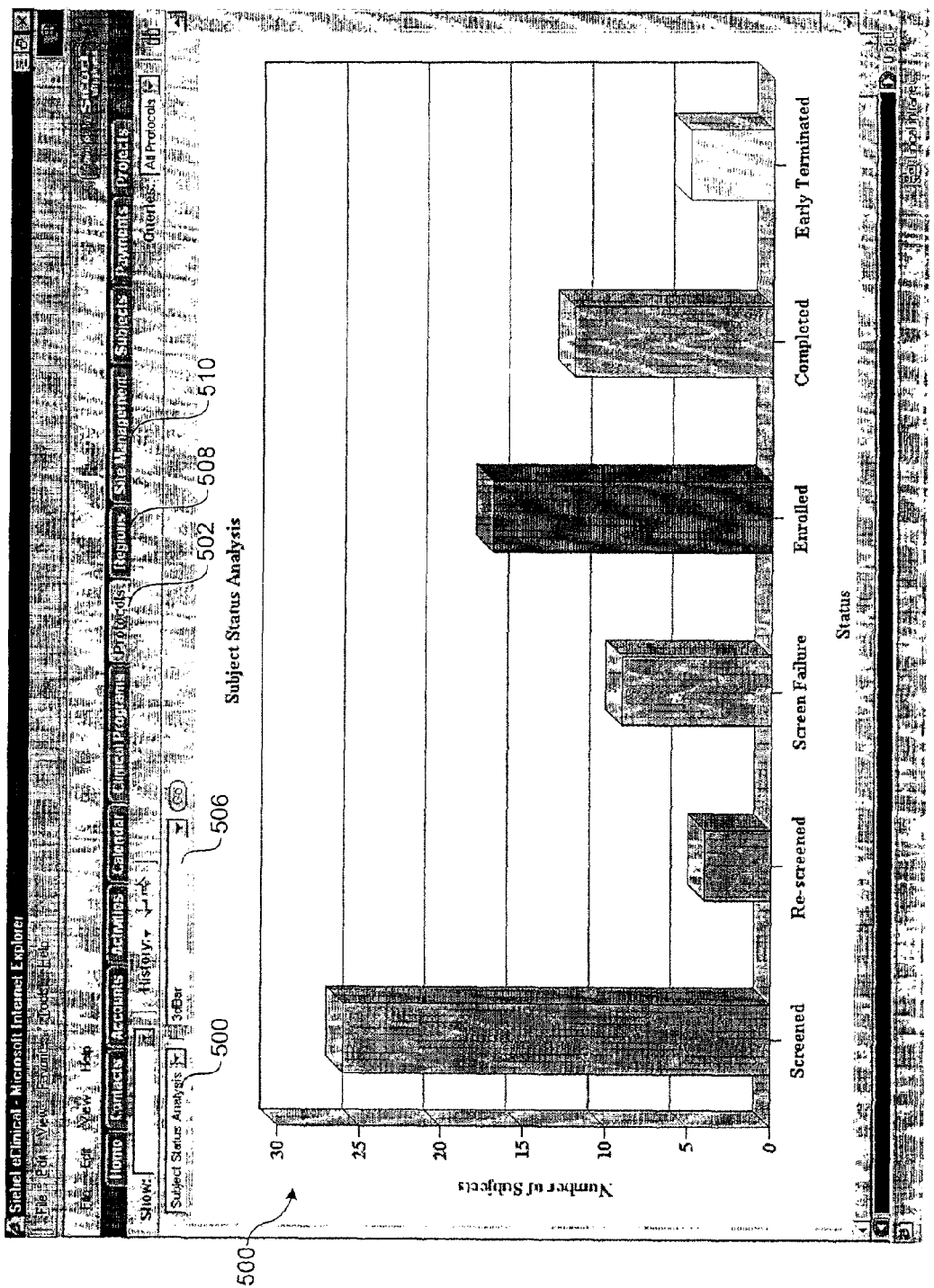
FIG. 16 is a representation of a subject status analysis chart that may be generated with the eClinical application based on subject enrollment data (generally) entered via the web portal.
Figure 17:
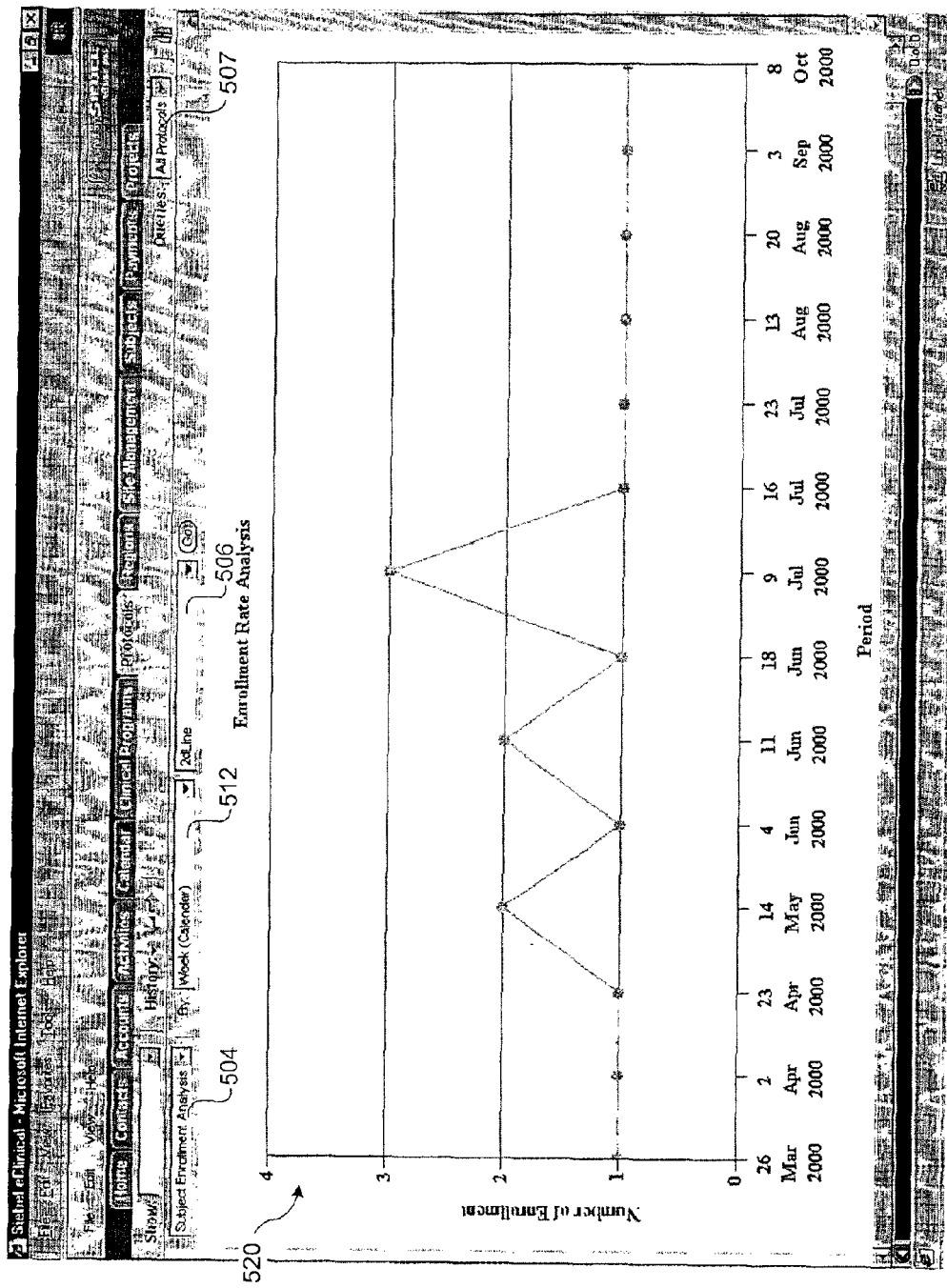
FIG. 17 is a representation of an enrollment rate analysis chart based on the subject enrollment data.

For example, a subject status analysis chart 500 that graphically portrays various types of subject enrollment status data is shown in FIG. 16. As used in the following discussions and the claims that follow, the term "enrollment status data" pertains to the various statuses clinical trial subjects may have, which may include "screened," "re-screened," "screen failure," "completed," "early terminated" or other customer-configured status in addition to having an "enrolled" status. By graphically portraying these various types of enrollment status, clinical trial administrators can quickly identify positive and negative status situations. For example, a relatively high number of early terminations may point to a need to modify a particular protocol, while a relatively high number of screen failures might indicate that the screening requirements are too strict.

The charts may also be configured to display data pertaining to certain status types in different colors for greater emphasis. For example, when a bar-type chart is selected for generation, a bar corresponding to the "enrolled" status may be displayed in an eye-catching color, such as red, while a more subtle color might be used for screen and re-screened statuses, such as green or blue.

The eClinical application provides several routes to navigate to the same chart. For example, if a user desires to view data aggregated across an entire protocol, the user merely needs to select a protocols tab 502, select a desired protocol (via its protocol number), select a chart view tab, and then select charting options, via either pull down menu options (not shown) or dropdown controls, such as a chart dataset dropdown control 504 and a chart type dropdown control 506. In addition, a queries dropdown control 507 allows queries to be saved and recalled in the future, wherein the values in the dropdown list comprise past queries that have been run and saved. Optionally, these queries may also include queries created by an administrator for all users to use. Once a chart pertaining to a given dataset is generated, other types of charts pertaining to the same dataset may be easily generated, such as line graph charts, splined curve charts, pie charts, etc.

In a similar manner, users can chart data across regions and individual sites. For example, to generate charts containing dataset pertaining to regions, the user would select a "Regions" tab 508, enter or select a protocol number corresponding to the protocol that chart is to pertain to, select a desired region, and then select the chart data and type options. Similarly, to chart data pertaining to an individual site, the user will select a "Site Management" tab 510, enter or select protocol and site identification information, and then select desired chart data and type options.

Another chart provided by graphically portrays enrollment rate analysis data. This type of chart, such as depicted by an enrollment rate analysis 2D line chart 520 in FIG. 1, reflects the number of subjects enrolled during various time intervals, such as weekly or monthly. This time, the chart view dropdown controls further include a period dropdown control 512, which is used to select the time interval between data points for the chart. As before, enrollment rate analysis charts can be generated to aggregate data across a given site, across a region, or across an entire protocol. This type of chart is not limited to "enrolled" status. Similar charts for Screened or other statuses are possible.

The dataset from which a particular chart is derived is retrieved from enterprise database 31 based on the various charting parameters and options. As discussed above, under the object manager-data manager architecture implemented by one embodiment of the system, the actual database structure is abstracted from the business components used to retrieve and store data in the enterprise database. Furthermore, this abstraction enables various database server software to be used to host the enterprise database.

In general, a SQL query will be generated by the data manager in response for a request of the chart dataset from a business component or business object. For example, suppose a subject enrollment rate chart is to be generated using a weekly time interval for a particular site. Pseudocode corresponding to an exemplary SQL query to return an appropriate result set for this requested chart based on the data model of FIG. 8 might look like:

SELECT Count(S.Subject_Initials), ROUND (SSS.status_update, WEEK) FROM SUBJECT S, PROTOCOL P, PROTOCOL_SITE PS, (SELECT Screening_ID, Status update from SUBJECT_STATUS SS where status ="enrolled" and Status_update =(Select MAX(Status_update) from SUBJECT_STATUS Screening_ID=SS.Screening_ID)) SSS
   WHERE S.Protocol_Site_ID =PS.Protocol_Site_ID
   AND PS.Protocol_Site_ID =Protocol_site_input
   AND P.Protocol_ID Protocol_number_input
   AND P.Protocol_ID =PS.Protocol_ID
   AND S.Screening_ID in (SELECT Screening_ID) from SSS
GROUP BY ROUND(SS.status_update, WEEK);

This query would return a count of the number of subjects enrolled for each week at a particular site based on input parameters identifying the protocol and site (bolded). A corresponding 2D line or bar chart could be build directly from the dataset. If appropriate, data filtering options (in the initial query, or to filter the returned dataset) may be implemented to limit the timeframe that is viewed at one time. In addition, the Y axis on the various charts may be automatically scaled based on some predetermined criteria, such as a maximum value in the dataset.

Exemplary Computer System for Practicing the Invention

Figure 18:
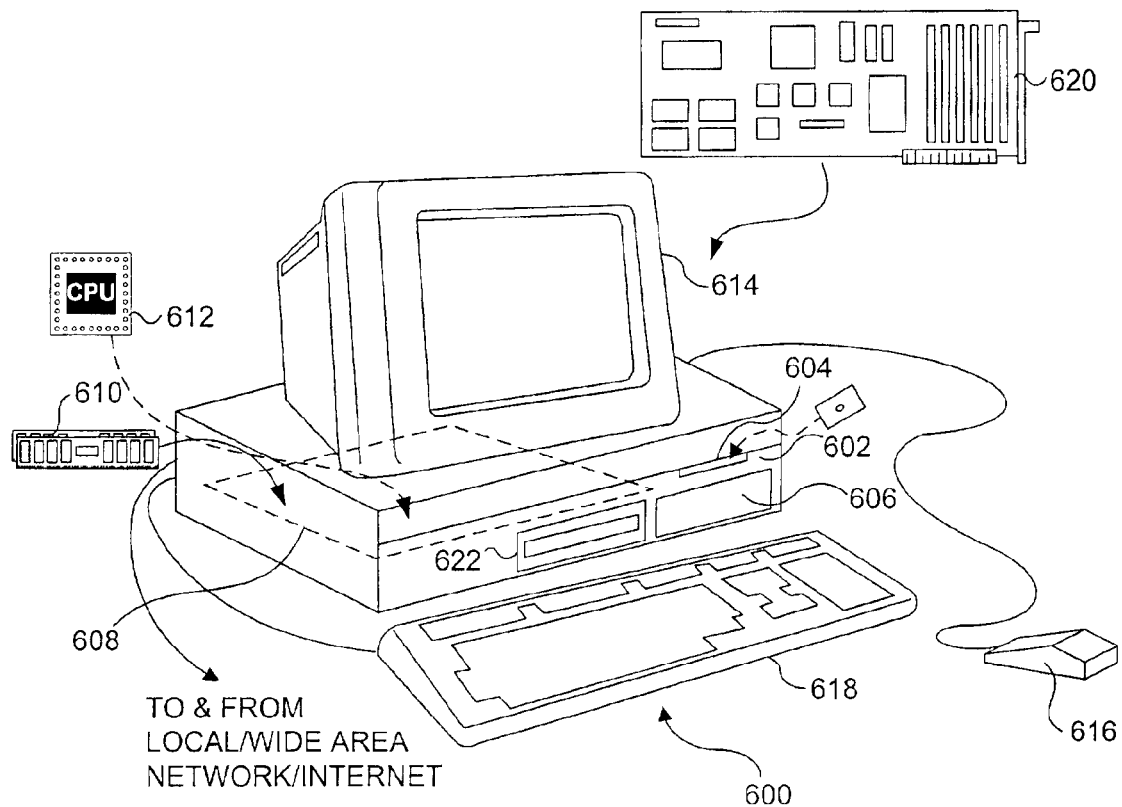
FIG. 18 is a schematic diagram illustrating an exemplary computer system that may be used to implement various client and server aspects of the invention.

With reference to FIG. 18, a generally conventional computer 600 is illustrated, which is suitable for use as client machines, application servers, and database servers in connection with practicing the present invention, and may be used for running client and server-side software comprising one or more software modules that implement the various operations of the invention discussed above. Examples of computers that may be suitable for client machines as discussed above include PC-class systems operating the Windows NT or Windows 2000 operating systems, Sun workstations operating the UNIX-based Solaris operating system, and various computer architectures that implement LINUX operating systems. Computer 600 is also intended to encompass various server architectures, as well as computers having multiple processors.

Computer 600 includes a processor chassis 602 in which are mounted a floppy disk drive 604, a hard drive 606, a motherboard 608 populated with appropriate integrated circuits including memory 610 and one or more processors (CPUs) 612, and a power supply (not shown), as are generally well known to those of ordinary skill in the art. It will be understood that hard drive 606 may comprise a single unit, or multiple hard drives, and may optionally reside outside of computer 600. A monitor 614 is included for displaying graphics and text generated by software programs and program modules that are run by the computer. A mouse 616 (or other pointing device) may be connected to a serial port (or to a bus port or USB port) on the rear of processor chassis 602, and signals from mouse 616 are conveyed to the motherboard to control a cursor on the display and to select text, menu options, and graphic components displayed on monitor 614 by software programs and modules executing on the computer. In addition, a keyboard 618 is coupled to the motherboard for user entry of text and commands that affect the running of software programs executing on the computer. Computer 600 also includes a network interface card 620 or built-in network adapter for connecting the computer to a computer network, such as a local area network, wide area network, or the Internet.

Computer 600 may also optionally include a compact disk-read only memory (CD-ROM) drive 622 into which a CD-ROM disk may be inserted so that executable files and data on the disk can be read for transfer into the memory and/or into storage on hard drive 606 of computer 600. Other mass memory storage devices such as an optical recorded medium or DVD drive may be included. The machine instructions comprising the software that causes the CPU to implement the functions of the present invention that have been discussed above will likely be distributed on floppy disks or CD-ROMs (or other memory media) and stored in the hard drive until loaded into random access memory (RAM) for execution by the CPU. Optionally, all or a portion of the machine instructions may be loaded via a computer network.

Although the present invention has been described in connection with a preferred form of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

What is claimed is:

1. A method comprising:
   enabling an administrator to define a plurality of clinical trial parameters through filling out fields in a set of computer forms;
   storing the clinical trial parameters in a central database;
   enabling clinical trial site personnel to enter subject enrollment data corresponding to at least one clinical trial defined by the clinical trial parameters via an Internet web portal;

storing the subject enrollment data in the central database substantially as it is entered in time; and generating a chart displaying selected data aggregated from the subject enrollment data to graphically portray subject enrollment attributes pertaining to a selected clinical trial from among said at least one clinical trial.

2. The method of claim 1, wherein the selected data are aggregated across an entire protocol corresponding to the selected clinical trial.

3. The method of claim 1, wherein the selected data correspond to an individual site that implements a protocol corresponding to a clinical trial.

4. The method of claim 1, wherein the administrator is enabled to define regions corresponding to a clinical trial protocol, each region corresponding to one or more sites that perform subject tests defined by a clinical trial protocol, and the selected data are aggregated across a selected region.

5. The method of claim 1, wherein the chart comprises an enrollment rate analysis chart that portrays a number of subjects newly enrolled for the selected clinical trial during each of a plurality of periodic intervals using a selected aggregation level.

6. The method of claim 5, wherein the selected aggregation level corresponds to one of a site, a region comprising a plurality of sites, or a protocol comprising all of the sites used to perform a protocol corresponding to the selected clinical trial.

7. The method of claim 1, wherein the chart comprises a subject status analysis chart that portrays a plurality of subject status totals pertaining to the selected clinical trial and corresponding to a selected aggregation level.

8. The method of claim 7, wherein the selected aggregation level corresponds to one of a site, a region comprising a plurality of sites, or a protocol comprising all of the sites used to perform a protocol corresponding to the selected clinical trial.

9. The method of claim 1, wherein the administrator is enabled to define said plurality of clinical trial parameters using a computer that has a dedicated connection to the central database.

10. The method of claim 1, wherein the administrator is enabled to define said plurality of clinical trial parameters using a computer that stores corresponding data in a local database, further comprising synchronizing the local database with the central database such that data pertaining to said plurality of clinical trial parameters are copied to the central database.

11. The method of claim 1, wherein the computer forms are generated by rendering applets on a browser.

12. The method of claim 1, wherein the Internet web portal is supported by an application server hosting a plurality of software modules, including an object manager that interacts with a web engine to generate webbased forms including a plurality of fields that enable users of the Internet web portal to enter the subject enrollment data corresponding to said at least one clinical trial and a data manager that interacts with the object manager and a database server that hosts the central database to store data corresponding to the plurality of fields in the web-based forms.

13. The method of claim 12, wherein the object manager includes a plurality of object classes and wherein the web-based forms comprise java-script based applets corresponding to a set of java-script object classes that substantially mirror respective object classes corresponding to the object manager.

14. The method of claim 1, further comprising:

providing a log-in mechanism to enable qualified users to access the Internet web portal;

identifying the user based on log-in data entered by the user that is authenticated against log-in information stored in the central database;

identifying any clinical trials the user is participating in as a member of an investigation team working on those clinical trials;

enabling the user to enter subject enrollment data pertaining to any clinical trials that are identified.

15. A method comprising:

defining parameters corresponding to a protocol for a clinical trial via a computer interface;

defining parameters corresponding to one or more sites that are used for conducting clinical trial tests based on the protocol via the computer interface;

storing the protocol and site parameters in a central database;

enabling clinical trial site personnel to enter subject enrollment data corresponding to the protocol via an Internet web portal;

storing the subject enrollment data in the central database substantially as it is entered in time via the Internet web portal;

generating a chart to graphically portray aggregated subject enrollment data pertaining to the protocol.

16. The method of claim 15, further comprising defining regions for the protocol, each region comprising one or more sites.

17. The method of claim 16, wherein the chart depicts subject enrollment data that are aggregated across a selected region.

18. The method of claim 15, wherein the chart depicts subject enrollment data that are aggregated across an individual site.

19. The method of claim 15, wherein the chart depicts subject enrollment data that are aggregated across all sites for the protocol.

20. The method of claim 15, wherein the chart comprises an enrollment rate analysis chart that portrays a number of subjects newly enrolled for one of a site, region, or protocol during each of a plurality of periodic intervals.

21. The method of claim 15 wherein the chart comprises a subject status analysis chart that portrays a plurality of subject status totals pertaining to a selected aggregation level of protocol sites.

22. The method of claim 21, wherein the selected aggregation level corresponds to one of an individual site, a region comprising a plurality of sites, or all of these sites defined for the protocol.

23. The method of claim 15, further comprising:

providing a log-in to enable qualified users to access the Internet web portal;

identifying the user based on log-in data stored in the central database;

identifying any protocols the user is participating in as a member of an investigation team working on those protocols;

enabling the user to enter subject enrollment data pertaining to any protocols that are identified.

24. The method of claim 15, wherein an administrator is enabled to define the protocol and site parameters using a computer that stores corresponding data in a local database, further comprising synchronizing the local database with the central database such that data pertaining to the protocol and site parameter are copied to the central database.

* * * * *